United States Patent [19]

Frobel et al.

[11] Patent Number: 5,089,487

[45] Date of Patent: Feb. 18, 1992

[54] CIRCULATION-ACTIVE DIBENZO[1,5]DIOXOCIN-5-ONES

[75] Inventors: Klaus Frobel; Jan-Bernd Lenfers; Peter Fey, all of Wuppertal; Andreas Knorr, Erkrath; Johannes-Peter Stasch, Wuppertal; Hartwig Müller, Velbert; Erwin Bischoff; Hans-Georg Dellweg, both of Wuppertal, all of Fed. Rep. of Germany

[73] Assignee: Bayer Aktiengesellschaft, Leverkusen, Fed. Rep. of Germany

[21] Appl. No.: 528,667

[22] Filed: May 24, 1990

[30] Foreign Application Priority Data

Jun. 13, 1989 [DE] Fed. Rep. of Germany ....... 3919255

[51] Int. Cl.$^5$ ................ A61K 31/655; A61K 31/365; C07D 321/00
[52] U.S. Cl. ................... 514/150; 514/450; 514/149; 549/267
[58] Field of Search ................ 549/267; 514/450, 149, 514/150

[56] References Cited

U.S. PATENT DOCUMENTS

| | | | |
|---|---|---|---|
| 3,639,612 | 2/1972 | DeLong et al. | 514/450 |
| 4,701,466 | 10/1987 | Purcell et al. | 514/450 |
| 4,751,238 | 6/1988 | Martin et al. | 514/450 |
| 4,940,726 | 7/1990 | Pettit et al. | 514/450 |

OTHER PUBLICATIONS

Sasea, T. et al, "Structure of Penicillide a New Metabolite Produced by a Pencillium Species", CA 82 125001a (1975).

Tetrahedron Letters, vol. 45, pp. 3941-3942 (1974).

*Primary Examiner*—Alan L. Rotman
*Assistant Examiner*—Amelia A. Owens
*Attorney, Agent, or Firm*—Sprung, Horn, Kramer & Woods

[57] ABSTRACT

Cardioactive compounds of the formula

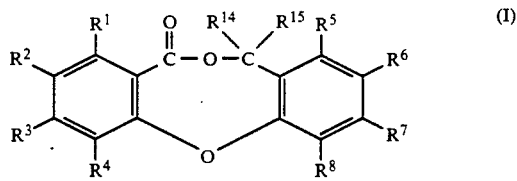

in which $R^1$ and $R^8$ and $R^{14}$ and $R^{15}$ can be hydrogen or various organic radicals.

14 Claims, No Drawings

CIRCULATION-ACTIVE DIBENZO[1,5]DIOXOCIN-5-ONES

The present invention relates to 7H-dibenzo[1,5]-dioxocin-5-ones, their use in medicaments and processes for their preparation, in particular their use in medicaments acting on the circulation.

In Tetrahedron Letters Vol. 45, 3941-3942 (1974), a natural substance having the name penicillide has already been mentioned by formula, the monomethyl ether of which is supposed to have a germination-inhibiting effect on Chinese cabbage. Extraction from the mycelium of a fungus of the species Penicillium which is not described clearly taxonomically is given as the preparation process. In the light of the insufficient disclosure of this publication, the preparation process is not reproducible and thus this natural substance is unavailable to the public.

By means of the present invention, reproducible processes for the preparation of these compounds are made available for the first time and, at the same time, their first pharmaceutical application is claimed.

The present invention relates to compounds of the general formula (I)

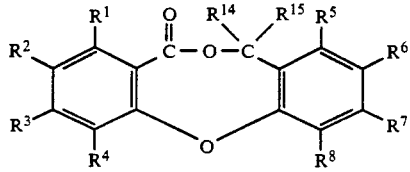

in which
$R^1$, $R^2$, $R^3$, $R^4$, $R^5$, $R^6$, $R^7$ and $R^8$ are identical or different and in each case
represent hydrogen or
represent straight-chain or branched alkylthio, alkyl, alkenyl or alkinyl in each case having up to 12 carbon atoms, which are optionally substituted by halogen, azido, imino, hydroxyl-substituted imino, hydroxyl, cyano, cycloalkyl having 3 to 8 carbon atoms, or by a 3- to 7-membered, saturated or unsaturated heterocycle having up to 4 heteroatoms from the series comprising nitrogen, sulphur or oxygen, or by aryl or aryloxy having 6 to 10 carbon atoms, which in turn may be monosubstituted to trisubstituted by identical or different substituents from the series comprising halogen, nitro, phenyl, phenoxy, cyano, straightchain or branched alkyl, alkoxy or alkoxycarbonyl in each case having up to 8 carbon atoms, or by a radical of the formula

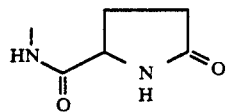

or by a group of the formula $-NR^9R^{10}$, $-COR^{11}$ or $-OR^{12}$, in which $R^9$ and $R^{10}$ are identical or different and in each case denote hydrogen, straight-chain or branched alkyl having up to 10 carbon atoms or aryl having 6 to 10 carbon atoms, or a group of the formula $-S(O)_pR^{13}$ $R^{11}$ denotes hydrogen, hydroxyl, straight-chain or branched alkyl or alkoxy having up to 10 carbon atoms, phenoxy, aryl having 6 to 10 carbon atoms or the group $-NR^9R^{10}$, in which $R^9$ and $R^{10}$ have the abovementioned meanings, $R^{12}$ denotes hydrogen, cycloalkyl having 3 to 8 carbon atoms, formyl, acyl having up to 8 carbon atoms, tetrahydropyranyl, trifluoromethoxy or a group of the formula $-S(O)_pR^{13}$, in which p denotes a number 1 or 2, $R^{13}$—denotes straight-chain or branched alkyl having up to 8 carbon atoms or the group $-NR^9R^{10}$, in which $R^9$ and $R^{10}$ have the abovementioned meanings, or $R^{12}$ denotes straight-chain or branched alkyl or alkenyl having up to 10 carbon atoms, which is optionally substituted by hydroxyl, halogen, cycloalkyl having 3 to 8 carbon atoms, alkoxy or alkoxycarbonyl having up to 8 carbon atoms, or by aryl having 6 to 10 carbon atoms, which in turn may be substituted by halogen, hydroxyl, alkyl, alkoxy or alkoxycarbonyl in each case having up to 8 carbon atoms, or nitro or cyano, or by a 3- to 7-membered, saturated or unsaturated heterocycle having up to 4 heteroatoms from the series comprising sulphur, oxygen or nitrogen or by a group of the formula $-NR^9R^{10}$, $-COR^{11}$ or $-OR^{12}$, in which $R^9$, $R^{10}$, $R^{11}$ and $R^{12}$ have the abovementioned meanings, or is substituted by a radical of the formula

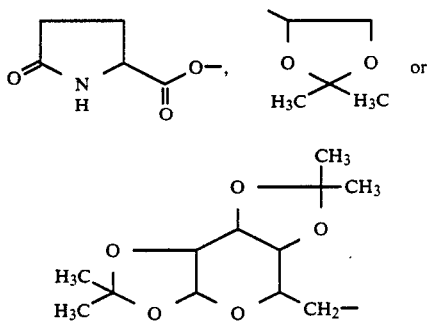

or denotes aryl having 6 to 10 carbon atoms, which is optionally substituted by halogen, hydroxyl, nitro or cyano, or $R^1$, $R^2$, $R^3$, $R^4$, $R^5$, $R^6$, $R^7$ and $R^8$ are identical or different and in each case
represent halogen, cyano, hydroxyl or nitro,
represent a 3- to 7-membered heterocycle having up to 4 heteroatoms from the series comprising sulphur, oxygen or nitrogen or pyridyl-methoidodide, or aryl having 6 to 10 carbon atoms, which in turn may be substituted by halogen, cyano, phenyl, nitro, straight-chain or branched alkyl or alkoxy in each case having up to 8 carbon atoms or hydroxyl, or
represent cycloalikenyl having 3 to 8 carbon atoms
represent a group of the formula $-NR^9R^{10}$, $-COR^{11}$ or $-OR^{12}$ in which $R^9$, $R^{10}$, $R^{11}$ and $R^{12}$ have the abovementioned meanings,
or $R^1$ and $R^2$, $R^2$ and $R^3$, $R^3$ and $R^4$, $R^5$ and $R^6$, $R^6$ and $R^7$, or $R^7$ and $R^8$ in each case together form a saturated or unsaturated 5- to 7-membered carbocycle which is optionally substituted by nitro, cyano, hydroxyl, straight-chain or branched alkyl having up to 8 carbon atoms, or by a group of the formula $-NR^9R^{10}$, $-COR^{11}$ or $-OR^{12}$, $R^{14}$ and $R^{15}$ are identical or different and in each case denote hydrogen, or straight-chain or branched alkyl having up to 10 carbon atoms, which is optionally substituted by halogen, nitro, cyano, hydroxyl or a group of the formula —NR$^9$R$^{10}$, —COR$^{11}$ or —OR$^{12}$, in which R$^9$, R$^{10}$, R$^{11}$ and R$^{12}$ have the abovementioned meanings, denote aryl having 6 to 10 carbon atoms, which is optionally substituted by nitro, cyano, halogen, alkyl, alkoxy or alkoxycarbonyl having up to 8 carbon atoms or by a group of the formula —NR$^9$R$^{10}$, in which R$^9$ and R$^{10}$ have the abovementioned meanings, or R$^{14}$ and R$^{15}$ together form a 5- to 7-membered, saturated or unsaturated carbocycle, and their physiologically acceptable salts.

It has been found that the compounds according to the invention surprisingly have an antihypertensive action and strongly stimulate the release of ANP and are thus suitable for combating hypertonia and in digitalis poisoning, and also in the treatment of cardiac insufficiency, cardiac arrhythmias and oedemas.

The physiologically acceptable acid addition salts of the compounds of the general formula (I) and the racemic forms, the antipodes and the diastereomeric mixtures are also preferably suitable for the novel application.

Preferred compounds of the general formula (I) are those in which

R$^1$, R$^2$, R$^3$, R$^4$, R$^5$, R$^6$, R$^7$ and R$^8$ are identical or different and in each case represent hydrogen or represent straight-chain or branched alkylthio, alkyl, alkenyl or alkinyl in each case having up to 10 carbon atoms, which are optionally monosubstituted to tetrasubstituted by identical or different radicals such as fluorine, chlorine, bromine, azido, imino, hydroxyl-substituted imino, hydroxyl, cyano, cyclopropyl, cyclopentyl, cyclohexyl, or by pyrryl, morpholino, piperidyl, oxiranyl or phenyl, which in turn may be monosubstituted to trisubstituted by identical or different substituents from the series comprising fluorine, chlorine, bromine, iodine, nitro, phenyl, phenoxy, cyano, straight-chain or branched alkyl, alkoxy or alkoxycarbonyl in each case having up to 6 carbon atoms, or by a radical of the formula

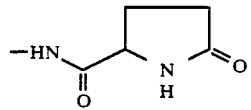

or are substituted by a group of the formula —NR$^9$R$^{10}$, —COR$^{11}$ or —OR$^{12}$, in which R$^9$ and R$^{10}$ are identical or different and in each case denote hydrogen, straight-chain or branched alkyl having up to 8 carbon atoms or phenyl, or a group of the formula —S(O)$_p$—R$^{13}$ R$^{11}$ denotes hydrogen, hydroxyl, straight-chain or branched alkyl or alkoxy having up to 8 carbon atoms, phenoxy, phenyl or the group —NR$^9$R$^{10}$, in which R$^9$ and R$^{10}$ have the abovementioned meanings, R$^{12}$ denotes hydrogen, cyclopropyl, cyclobutyl, cyclopentyl, cyclohexyl, cycloheptyl, formyl, acyl having up to 6 carbon atoms, tetrahydropyranyl, trifluoromethoxy or a group of the formula —S(O)$_p$—R$^{13}$, in which p denotes a number 1 or 2, R$^{13}$—denotes straight-chain or branched alkyl having up to 6 carbon atoms or the group —NR$^9$R$^{10}$, in which R$^9$ and R$^{10}$ have the abovementioned meanings, or R$^{12}$ denotes straight-chain or branched alkyl or alkenyl having up to 8 carbon atoms, which is optionally monosubstituted to tetrasubstituted by identical or different radicals such as hydroxyl, fluorine, chlorine, bromine, cyclopropyl, cyclopentyl, cyclohexyl, alkoxy or alkoxycarbonyl having up to 6 carbon atoms or by phenyl which may in turn be substituted by fluorine, chlorine, bromine, hydroxyl, alkyl, alkoxy or alkoxycarbonyl in each case having up to 6 carbon atoms, nitro or cyano, or is substituted by oxiranyl, pyrimidyl, pyridyl or by a group of the formula —NR$^9$R$^{10}$, —COR$^{11}$ or —OR$^{12}$, in which R$^9$, R$^{10}$, R$^{11}$ and R$^{12}$ have the abovementioned meanings, or is substituted by a radical of the formula

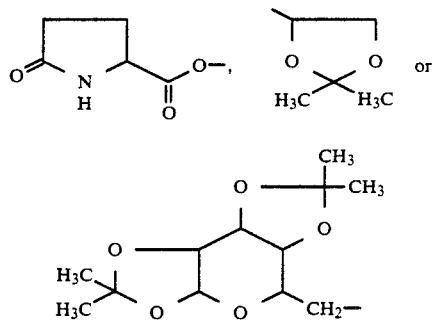

or

R$^1$, R$^2$, R$^3$, R$^4$, R$^5$, R$^6$, R$^7$ and R$^8$ are identical or different and in each case represent fluorine, chlorine, bromine, iodine, cyano, hydroxyl, nitro, pyridylmethoiodide or, furyl, 2,3-dihydrofuryl, pyridyl, thienyl, dihydropyranyl or thiazolyl, oxiranyl or phenyl, which are optionally substituted by fluorine, chlorine, bromine, phenyl, straight-chain or branched alkyl or alkoxy having up to 6 carbon atoms or hydroxyl, or represent a group of the formula —NR$^9$R$^{10}$, —COR$^{11}$ or OR$^{12}$, represent cyclobutenyl, cyclopentenyl or cyclohexenyl in which R$^9$, R$^{10}$, R$^{11}$ and R$^{12}$ have the abovementioned meanings, or R$^1$ and R$^2$, R$^2$ and R$^3$, R$^3$ and R$^4$, R$^5$ and R$^6$, R$^6$ and R$^7$, or R$^7$ and R$^8$ together represent phenyl, cyclopentyl or cyclohexyl, R$^{14}$ and R$^{15}$ are identical or different and in each case denote hydrogen, or straight-chain or branched alkyl having up to 8 carbon atoms, which is optionally substituted by fluorine, chlorine, bromine, cyano, hydroxyl or by a group of the formula —NR$^9$R$^{10}$, —COR$^{11}$ or —OR$^{12}$, in which R$^9$, R$^{10}$, R$^{11}$ and R$^{12}$ have the abovementioned meanings, or denote phenyl which is optionally substituted by nitro, cyano, fluorine, chlorine, bromine, alkyl, alkoxy or alkoxycarbonyl having up to 6 carbon atoms or by the group of the formula —NR$^9$R$^{10}$, in which R$^9$ and R$^{10}$ have the abovementioned meanings, and their physiologically acceptable salts.

Compounds of the general formula (1) which may be particularly preferably mentioned are those in which R$^1$, R$^2$, R$^3$, R$^4$, R$^5$, R$^6$, R$^7$ and R$^8$ are identical or different and in each case represent hydrogen or represent straight-chain or branched alkylthio, alkyl, alkenyl or alkinyl in each case having up to 8 carbon atoms, which are optionally monosubstituted to tetrasubstituted by identical or different radicals such as fluorine, chlorine, bromine, iodine, azido, imino, hydroxyl-substituted imino, hydroxyl, cyclopropyl, cyclopentyl, cyclohexyl, or are substituted by morpholino, piperidyl, pyrryl, oxiranyl or phenyl, which in turn may be monosubstituted to trisubstituted by identical or different substituents from the series comprising fluorine, chlorine, phenyl, phenoxy or by straight-chain or branched alkyl or alkoxy having up to 4 carbon atoms, or are substituted by a radical of the formula

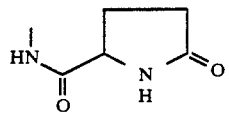

or by a group of the formula —NR$^9$R$^{10}$, —COR$^{11}$ or —OR$^{12}$, in which R$^9$ and R$^{10}$ are identical or different and in each case denote hydrogen, straight-chain or branched alkyl having up to 6 carbon atoms or phenyl or a group of the formula —S(O)$_p$—R$^{13}$ R$^{11}$ denotes hydrogen, hydroxyl, trifluoromethyl, straight-chain or branched alkyl, or alkoxy having up to 6 carbon atoms, phenoxy, phenyl or the group —NR$^9$R$^{10}$ in which R$^9$ and R$^{10}$ have the abovementioned meanings, R$^{12}$ denotes hydrogen, cyclopropyl, cyclopentyl, cyclohexyl, cycloheptyl, formyl, acyl having up to 4 carbon atoms, tetrahydropyranyl, trifluoromethoxy or a group of the formula —S(O)$_p$—R$^{13}$, in which p denotes a number 1 or 2, R$^{13}$—denotes straight-chain or branched alkyl having up to 4 carbon atoms, or denotes straight-chain or branched alkyl or alkenyl having up to 6 carbon atoms, which is optionally monosubstituted to trisubstituted by identical or different radicals such as hydroxyl, fluorine, chlorine, bromine, cyclopropyl, cyclopentyl, cyclohexyl, alkoxy or alkoxycarbonyl having up to 4 carbon atoms or by phenyl which may in turn be substituted by fluorine, chlorine, hydroxyl or alkoxy having up to 4 carbon atoms, or is substituted by oxiranyl or by a group of the formula —NR$^9$R$^{10}$, —COR$^{11}$ or —OR$^{12}$, in which R$^9$, R$^{10}$, R$^{11}$ and R$^{12}$ have the abovementioned meanings, or is substituted by a radical of the formula

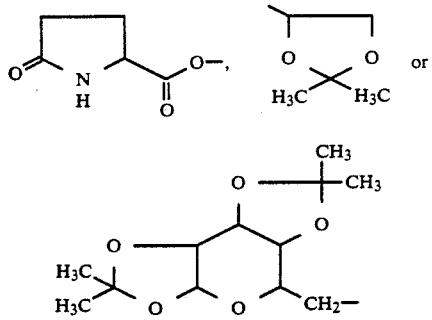

or
R$^1$, R$^2$, R$^3$, R$^4$, R$^5$, R$^6$, R$^7$ and R$^8$ are identical or different and in each case
represent fluorine, chlorine, bromine, iodine, hyroxyl, nitro or pyridyl-methoidodide or represent phenyl, furyl, 2,3-dihydrofuryl, pyridyl, thienyl, dihydropyranyl thiazolyl or oxiranyl which may in turn be substituted by fluorine, chlorine, methyl, isopropyl, phenyl or ethoxy, represent a group of the formula —NR$^9$R$^{10}$, —COR$^{11}$ or —OR$^{12}$, in which R$^9$, R$^{10}$, R$^{11}$ and R$^{12}$ have the abovementioned meanings, R$^{14}$ and R$^{15}$ are identical or different and denote hydrogen, straight-chain or branched alkyl having up to 6 carbon atoms of phenyl, and their physiologically acceptable salts.

The invention relates in particular to new compounds of the general formula (Ia)

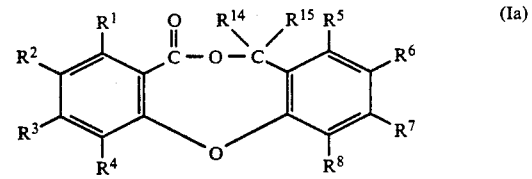

in which

R$^1$, R$^2$, R$^3$, R$^4$, R$^5$, R$^6$, R$^7$ and R$^8$ are identical or different and in each case
represent hydrogen or
represent straight-chain or branched alkyl, alkylthio, alkenyl or alkinyl in each case having up to 12 carbon atoms, which are optionally substituted by halogen, azido, imino, hydroxyl-substituted imino, hydroxyl, cyano, cycloalkyl having 3 to 8 carbon atoms, or by a 3- to 7-membered, saturated or unsaturated heterocycle having up to 4 heteroatoms from the series comprising nitrogen, sulphur or oxygen, or by aryl or aryloxy having 6 to 10 carbon atoms, which may in turn be monosubstituted to trisubstituted by identical or different substituents from the series comprising halogen, nitro, phenyl, phenoxy, cyano, straight-chain or branched alkyl, alkoxy or alkoxycarbonyl in each case having up to 8 carbon atoms, or are substituted by a radical of the formula

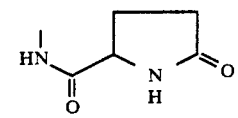

or by a group of the formula —NR$^9$R$^{10}$, —COR$^{11}$ or —OR$^{12}$, in which R$^9$ and R$^{10}$ are identical or different and in each case denote hydrogen, straight-chain or branched alkyl having up to 10 carbon atoms or aryl having 6 to 10 carbon atoms or a group of the formula —S(O)$_p$—R$^{13}$, R$^{11}$ denotes hydrogen, hydroxyl, straight-chain or branched alkyl or alkoxy having up to 10 carbon atoms, phenoxy, aryl having 6 to 10 carbon atoms or the group —NR$^9$R$^{10}$, in which R$^9$ and R$^{10}$ have the abovementioned meanings, R$^{12}$ denotes hydrogen, cycloalkyl having 3 to 8 carbon atoms, formyl, acyl having up to 8 carbon atoms, tetrahydropyranyl, trifluoromethoxy or a group of the formula —S(O)$_p$R$^{13}$, in which p denotes a number 1 or 2, R$^{13}$—denotes straight-chain or branched alkyl having up to 8 carbon atoms or the group —NR$^9$R$^{10}$, in which R$^9$ and R$^{10}$ have the abovementioned meanings, or R$^{12}$ denotes straight-chain or branched alkyl or alkenyl having up to 10 carbon atoms, which is optionally substituted by hydroxyl, halogen, cycloalkyl having 3 to 8 carbon atoms, alkoxy or alkoxycarbonyl having up to 8 carbon atoms, or by aryl having 6 to 10 carbon atoms, which in turn may be substituted by halogen, hydroxyl, alkyl, alkoxy or alkoxycarbonyl in each case having up to 8 carbon atoms, nitro or cyano, or is substituted by a 3- to 7-membered saturated or unsaturated heterocycle having up to 4 heteroatoms from the series comprising sulphur, oxygen or nitrogen or by a group of the formula —$NR^9R^{10}$, —$COR^{11}$ or —$OR^{12}$, in which $R^9$, $R^{10}$, $R^{11}$ and $R^{12}$ have the abovementioned meanings, or is substituted by a radical of the formula

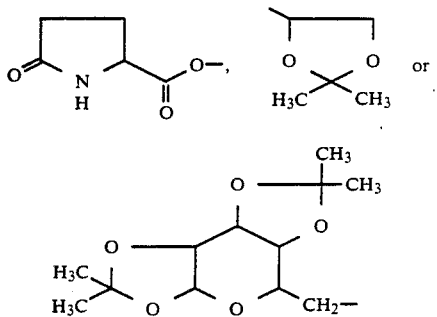

or denotes aryl having 6 to 10 carbon atoms, which is optionally substituted by halogen, hydroxyl, nitro or cyano, or $R^1$, $R^2$, $R^3$, $R^4$, $R^5$, $R^6$, $R^7$ and $R^8$ are identical or different and represent halogen, cyano, hydroxyl, nitro, or represent a 3- to 7-membered heterocycle having up to 4 heteroatoms from the series comprising sulphur, oxygen or nitrogen or pyridyl-methoiodide or, aryl having 6 to 10 carbon atoms, which in turn may be substituted by halogen, cyano, phenyl, nitro, straight-chain or branched alkyl or alkoxy in each case having up to 8 carbon atoms or hydroxyl, or represent cycloalkenyl having 3 to 8 carbon atoms represent a group of the formula —$NR^9R^{10}$, —$COR^{11}$ or —$OR^{12}$, in which $R^9$, $R^{10}$, $R^{11}$ and $R^{12}$ have the abovementioned meanings, or $R^1$ and $R^2$, $R^2$ and $R^3$, $R^3$ and $R^4$, $R^5$ and $R^6$, $R^6$ and $R^7$, or $R^7$ and $R^8$ in each case together form a saturated or unsaturated 5- to 7-membered carbocycle which is optionally substituted by nitro, cyano, hydroxyl, straight-chain or branched alkyl having up to 8 carbon atoms, or by a group of the formula —$NR^9R^{10}$, —$COR^{11}$ or —$OR^{12}$, $R^{14}$ and $R^{15}$ are identical or different and in each case denote hydrogen, or straight-chain or branched alkyl having up to 10 carbon atoms, which is optionally substituted by halogen, nitro, cyano, hydroxyl or a group of the formula —$NR^9R^{10}$, —$COR^{11}$ or —$OR^{12}$, in which $R^9$, $R^{10}$, $R^{11}$ and $R^{12}$ have the abovementioned meanings, or denote aryl having 6 to 10 carbon atoms, which is optionally substituted by nitro, cyano, halogen, alkyl, alkoxy or alkoxycarbonyl having up to 8 carbon atoms or by a group of the formula —$NR^9R^{10}$, in which $R^9$ and $R^{10}$ have the abovementioned meanings, or $R^{14}$ and $R^{15}$ together form a 5- to 7-membered, saturated or unsaturated carbocycle, with the proviso that a) $R^8$ may not denote hydroxyl, methoxy or acetyl if $R^1$ represents methoxy, $R^3$, $R^4$, $R^5$, $R^7$, $R^{14}$ and $R^{15}$ represent hydrogen, $R^6$ represents methyl and $R^2$ represents the group

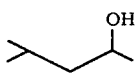

or b) $R^5$ and $R^7$ may not denote bromine and $R^8$ may not denote hydroxyl if $R^1$ represents methoxy, $R^3$, $R^4$, $R^{14}$ and $R^{15}$ represent hydrogen, $R^6$ represents methyl and $R^2$ represents the group

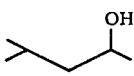

or c) $R^8$ may not denote methoxy if, $R^1$ represents methoxy, $R^3$, $R^4$, $R^5$, $R^7$, $R^{14}$ and $R^{15}$ represent hydrogen, $R^6$ represents methyl and $R^2$ represents the group

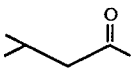

or d) $R^1$ may not denote methoxy if $R^3$, $R^4$, $R^5$, $R^6$, $R^{14}$ and $R^{15}$ represent hydrogen and $R^2$ represents the group of the formula

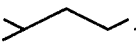

The new compounds of the formula (I) and the formula (Ia) according to the invention show an unforeseeable, useful spectrum of pharmacological action. They influence the release of ANP, the contractility of the heart, the tone of the smooth musculature and the electrolyte and fluid balance and additionally act either partially or completely as digitalis antagonists or digitalis agonists.

They can therefore be employed in medicaments for pathologically altered blood pressure, in particular as antihypertensives, for the treatment of cardiac insufficiency, and as coronary therapeutics or a therapeutic in digitalis poisoning.

Moreover, they can be employed for the treatment of cardiac arrhythmias, renal insufficiency, cirrhosis of the liver, ascites, lung oedema, cerebral oedema, oedema of pregnancy or glaucoma.

The compounds of the general formulae (I) and (Ia) according to the invention exist in stereoisomeric forms which behave either as image and mirror image (enantiomers) or which do not behave as image and mirror image (diastereomers). The invention relates both to the antipodes and to the racemic forms as well as the diastereomeric mixtures. The racemic forms, like the diastereomers, can be separated in a known manner into the stereoisomerically uniform constituents [cf. E. L. Eliel, Stereochemistry of Carbon Compounds, McGraw Hill, 1962].

Physiologically acceptable salts may be salts of the compounds of the general formulae (I) and (Ia) according to the invention with inorganic or organic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid phenylsulphonic acid, toluenesulphonic acid or naphthalenedisulphonic acid.

The compounds of the general formula (I) or (Ia) according to the invention are obtained by a process in which

[A] compounds of the general formula (II)

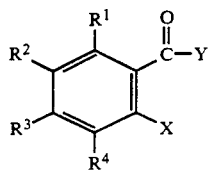

(II)

in which $R^1$, $R^2$, $R^3$ and $R^4$ have the abovementioned meanings,

X—represents fluorine, chlorine, bromine or iodine and

Y—represents $(C_1-C_6)$-alkoxy or aryloxy having 6 to 10 carbon atoms, are condensed with compounds of the general formula (III)

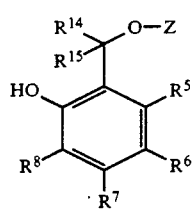

(III)

in which $R^5$, $R^6$, $R^7$, $R^8$, $R^{14}$ and $R^{15}$ have the abovementioned meanings and Z—represents a typical hydroxyl protecting group, such as, for example, tetrahydropyranyl, or compounds of the general formula (IIa)

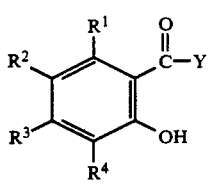

(IIa)

in which $R^1$, $R^2$, $R^3$, $R^4$ and Y have the abovementioned meanings, are condensed with compounds of the general formula (IIIa)

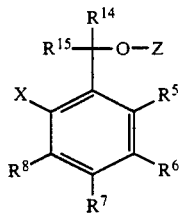

(IIIa)

in which $R^5$, $R^6$, $R^7$, $R^8$, $R^{14}$, $R^{15}$, X and Z have the abovementioned meanings, in inert solvents with elimination of hydrohalic acids, such as, for example, hydrogen bromide, to give compounds of the general formula (IV)

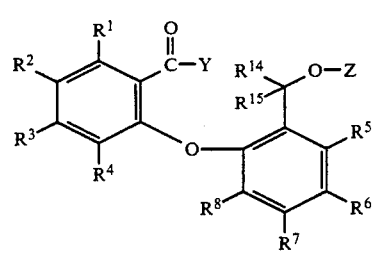

(IV)

in which $R^1$, $R^2$, $R^3$, $R^4$, $R^5$, $R^6$, $R^7$, $R^8$, $R^{14}$, $R^{15}$, Y and Z have the abovementioned meanings, then the hydroxyl group is deblocked by the customary method and the compound is cyclized with elimination of water, it being possible to introduce the substituents $R^1$, $R^2$, $R^3$, $R^4$, $R^5$, $R^6$, $R^7$, $R^8$, $R^{14}$, and $R^{15}$ into the compounds of the general formulae (II), (IIa), (III) and (IIIa) both before the condensation and after the cyclization to the compounds of the general formula (IV) by known methods, such as, for example, by alkylation, acylation, substitution, addition, elimination, rearrangement, oxidation, radical reaction or reduction and, if appropriate, subsequently to convert them into other functional groups, or by a process in which

[B] starting from the natural substance of the formula (Ib)

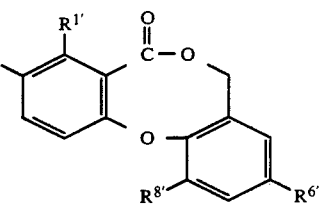

(Ib)
(known as "penicillide")

in which $R^{1'}$ represents methoxy, $R^{2'}$ represents the group

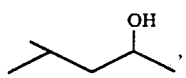

$R^{6'}$ represents methyl and $R^{8'}$ represents hydroxyl, the substituents $R^1$, $R^2$, $R^3$, $R^4$, $R^5$, $R^6$, $R^7$, $R^8$, $R^{14}$, and $R^{15}$ are introduced by the customary methods mentioned in process [A] and cited in the following by way of example, such as, for example, rearrangement, alkylation, acylation, addition, elimination, oxidation, radical reaction or reduction, in inert solvents, if appropriate in the presence of auxiliaries, such as, for example, bases, acids, catalysts or activating reagents, and these, as also the substituents $R^{1'}$, $R^{2'}$, $R^{6'}$ and $R^{8'}$, are converted into other functional groups.

As suitable customary methods, the following reactions may be mentioned by way of example:

a) the natural substance of the formula (Ib) or suitable derivatives which have been prepared by the method described in process [A] are reacted once or several times with compounds of the general formula (V)

$$R—D \qquad (V)$$

in which

R corresponds to the scope of meaning of one of the substituents $R^1$-$R^{15}$ cited above, but does not represent hydrogen, and D denotes a leaving group such as, for example, chlorine, bromine, iodine, $—SO_2—CH_3$ or $—SO_2—(C_6H_5)—p—CH_3$, in inert solvents, if appropriate in the presence of auxiliaries such as, for example, bases, acids or catalysts, or b) compounds of the formula (Ib) or suitable derivatives are reacted, for example, with amines, hydrazoic acid and ethyl azodicarboxylate, acetic acid, acetic anhydride, tetrahydropyran, thionyl chloride, methanesulphonyl chloride, 2-pyrrolidone-5-carboxylic acid or hydroxylamine in inert solvents, if appropriate in the presence of auxiliaries such as bases or catalysts, or c) are reacted with Grignard reagents of the general formula (VI)

$$R—Mg—Br \qquad (VI)$$

in which R has the abovementioned meaning, in inert solvents, or d) are halogenated with compounds of the general formula (VII)

$$E—Hal \qquad (VII)$$

in which

Hal represents fluorine, chlorine, bromine or iodine and

E— represents one of the substituents $R^1$-$R^{15}$ cited above having the meaning fluorine, chlorine, bromine or iodine or represents the radical $—CH_2—NO_2$, in inert solvents and, if appropriate, subsequently either introducing double bonds by elimination according to known methods, if appropriate carrying out an epoxidation and if appropriate adding on a reduction, oxidation or hydrolysis by a customary method, and thus introducing the substituents $R^1$-$R^{15}$ into the compounds of the general formula (Ib) and suitable derivatives, or converting the substituents $R^{1'}$, $R^{2'}$, $R^{6'}$ and $R^{8'}$ into other functional groups.

Depending on the type of starting materials used, the synthesis variations for the compounds according to the invention can be represented by the following equations:

[A]

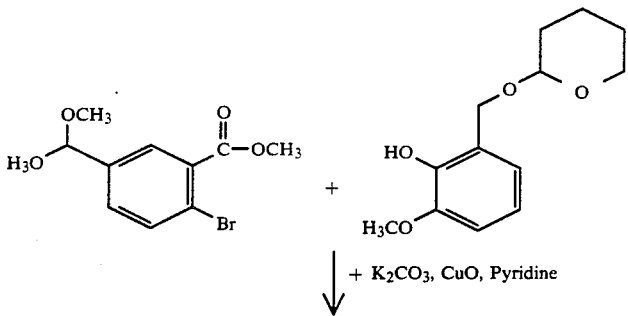

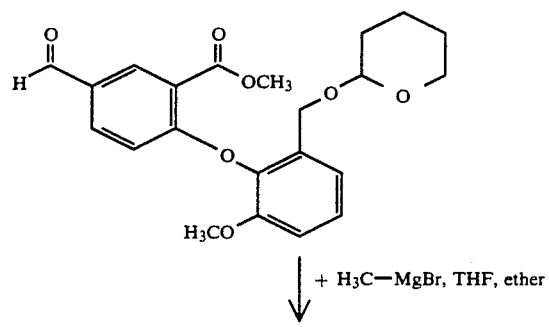

-continued
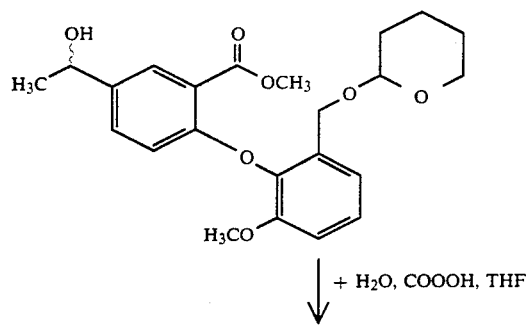
↓ + H₂O, COOOH, THF
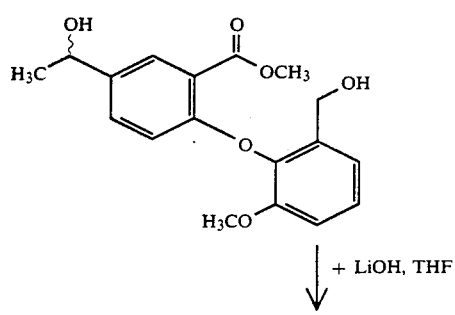
↓ + LiOH, THF
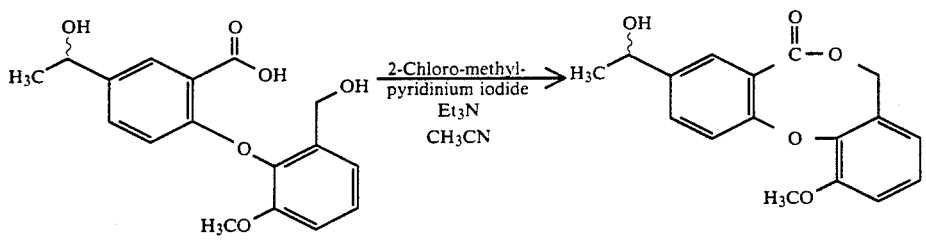
[B]
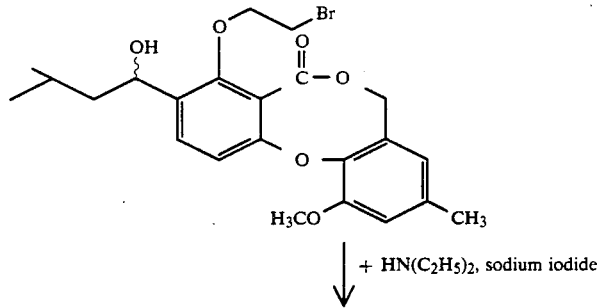
↓ + HN(C₂H₅)₂, sodium iodide
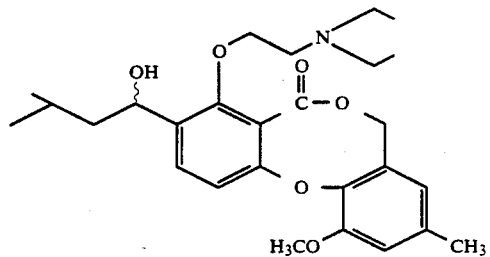

-continued
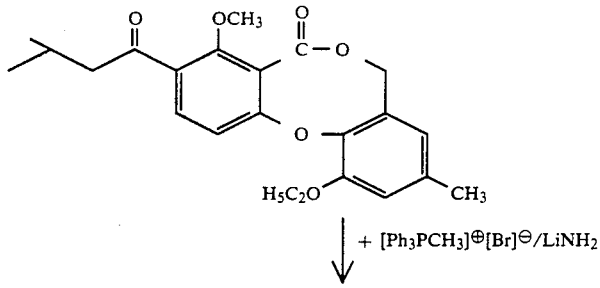
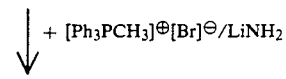
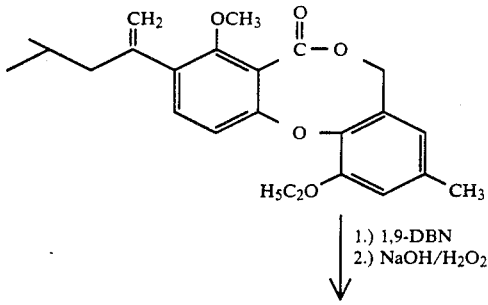
1.) 1,9-DBN
2.) NaOH/H₂O₂
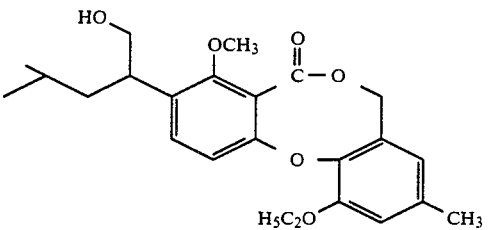
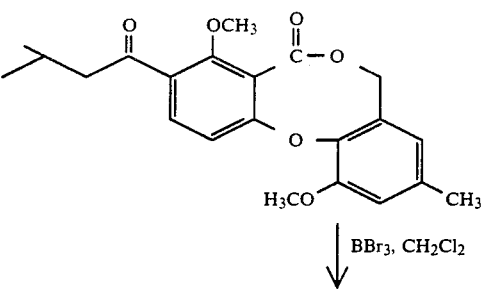
BBr₃, CH₂Cl₂
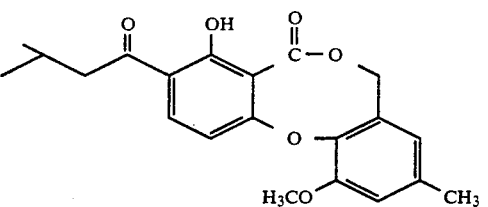
C₂H₅—I, K₂CO₃ / DMF
NaCNBH₃, THF, CH₃COOH
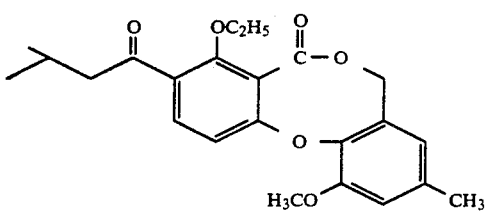
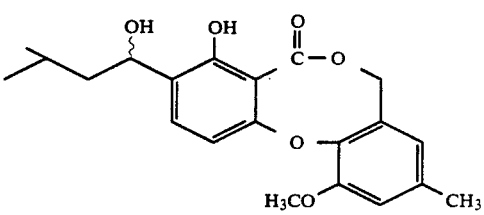
[B]
[B]

-continued

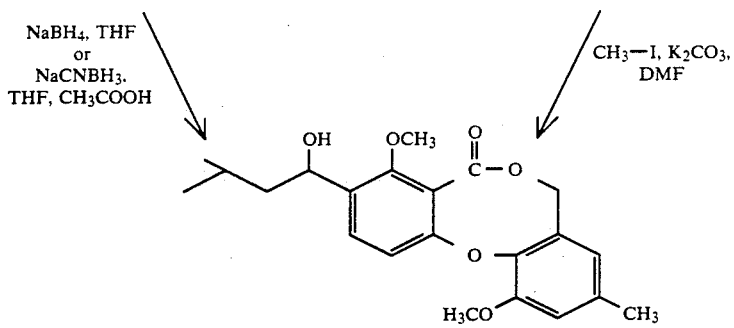

Processes [A]–[B]

Solvents for the processes [A] and [B] which can be used here are the customary organic solvents which do not change under the reaction conditions. These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoramide, or carboxylic acids such as acetic acid or propionic acid, or dimethyl sulphoxide, acetonitrile, ethyl acetate, or halogenated hydrocarbons such as methylene chloride, chloroform or carbon tetrachloride, or pyridine, picoline or N-methylpiperidine. Mixtures of the solvents mentioned can also be used.

The reaction temperatures can be varied within a relatively wide range in all processes. In general, the reaction is carried out between −20° C. and +200° C., preferably between +20° C. and +100° C., in particular at the boiling point of the respective solvent.

The reactions can be carried out at normal pressure, but also at elevated or reduced pressure. In general, the reaction is carried out at normal pressure.

When carrying out process variants A and B according to the invention, the ratio of the substances participating in the reaction is arbitrary. In general, however, the reaction is carried out using equimolar amounts of the reactants. The isolation and purification of the substances according to the invention is preferably carried out in such a way that the solvent is removed by distillation in vacuo and the residue, which may only be obtained in crystalline form after ice-cooling, is recrystallized from a suitable solvent. In some cases, it may be necessary to purify the compounds according to the invention by chromatography.

Suitable bases are the customary inorganic or organic bases. These preferably include alkali metal hydroxides such as, for example, sodium hydroxide, lithium hydroxide or potassium hydroxide, or alkali metal carbonates such as sodium carbonate or potassium carbonate, or alkali metal alkoxides such as, for example, sodium methoxide or potassium methoxide, or sodium ethoxide or potassium ethoxide, or organic amines such as triethylamine, picoline or N-methylpiperidine, or 2-chloro-N-methylpyridinium iodide, or amides such as sodium amide, lithium amide, lithium diisopropylamide, or organometallic compounds such as butyllithium or phenyllithium.

Catalysts employed for individual process variants are, for example, copper salts or oxides, preferably copper oxide and copper(II) acetate, or alkali metal iodides such as sodium iodide or potassium iodide, which are added to the reaction mixture in an amount from 0.5 to 150 equimolar, preferably 5 to 50 equimolar.

Activating reagents which may be added are, for example, azodicarboxylic acids or triphenylphosphine, in molar ratios or in excess.

The condensation described in process [A] is carried out in one of the inert solvents cited above under the action of a base, preferably in pyridine with potassium carbonate, while for the cyclization, acetonitrile, triethylamine and 2-chloro-N-methylpyridinium iodide are preferably employed.

Auxiliaries employed are preferably condensing agents, in particular if the carboxyl group is activated as the anhydride. Preferred here are the customary condensing agents such as carbodiimides, for example N,N'-diethyl-, N,N'-dipropyl-, N,N'-diisopropyl- or N,N'-dicyclohexylcarbodiimide, N-(3-dimethylaminoisopropyl)-N'-ethylcarbodiimide hydrochloride or 2-chloro-N-methylpyridinium iodide.

The introduction and removal of the hydroxyl protecting group is carried out by known methods [Th. Greene, "Protective Groups in Organic Synthesis", 1st Edition, J. Wiley & Sons, New York, 1981]. The protecting groups can be removed, for example, by acidic or basic hydrolysis or by hydrogenolysis.

The alkylation is carried out in one of the abovementioned inert solvents, preferably in dimethylformamide in the presence of potassium carbonate.

The reduction is in general carried out using metal hydrides or borohydrides, those preferred being sodium borohydride and sodium cyanoborohydride in inert solvents such as ethers, preferably in tetrahydrofuran, diethyl ether or dioxane, in a temperature range from −20° C. to +100° C., preferably from 0° C. to +50° C. at normal pressure.

The reduction is additionally possible by means of hydrogenation in inert solvents such as alcohols, for example methanol, ethanol, propanol or isopropanol in the presence of a noble metal catalyst such as platinum, palladium, palladium on animal charcoal or Raney nickel, in a temperature range from 0° C. to +150° C., preferably from room temperature to +100° C. at normal pressure or elevated pressure.

The reduction of carbonyl groups to hydrocarbons in general proceeds using reducing agents, such as zinc amalgam and acids such as hydrochloric acid or using hydrazine hydrate and bases such as sodium hydroxide or potassium hydroxide in the abovementioned solvents, preferably in ethers such as tetrahydrofuran or diethyl ether. Aldoximes and ketoximes are in general reduced to the corresponding amines using the abovementioned metal hydrides, preferably using lithium aluminum hydride, or using zinc and acetic acid, hydroboric acid, sodium in alcohols or by the abovementioned catalytic hydrogenation.

The reduction of alkoxycarbonyl groups to alcohol groups is in general carried out using hydrides, preferably using lithium aluminum hydride in inert solvents such as ethers, hydrocarbons or halogenated hydrocarbons or their mixtures, preferably in ethers such as, for example, diethyl ether, tetrahydrofuran or dioxane in a temperature range from 0° C. to +150° C., preferably from +20° C. to +100° C. at normal pressure.

The oxidation of alcohols to aldehydes and ketones is in general carried out using oxidizing agents such as dichromate, potassium permanganate, bromine, manganese dioxide, dipyridine-chromium(VI) oxide, pyridine dichromate, dimethylpyrazole-CrO$_3$ complex, silver carbonate on celite, iodosobenzene, lead tetraacetatepyridine, pyridinium chlorochromate or the Jones reagent, preferably using pyridinium chlorochromate in the abovementioned solvents, preferably in a temperature range from −20° C. to +100° C., preferably from 0° C. to +50° C. at normal pressure.

The Wittig reactions in general take place by reaction with tetraalkyl- or aryl-substituted phosphonium halides, preferably using triphenylmethylphosphonium bromide, in inert solvents such as ethers, preferably using tetrahydrofuran, in the presence of a base, preferably lithium amide, in a temperature range from −10° C. to +100° C., preferably at room temperature and at normal pressure.

The substitution reactions in general take place in the abovementioned inert solvents or in water, preferably in water, formic acid, methanol, ethanol, dimethylformamide or mixtures thereof, if appropriate in the presence of one of the abovementioned bases or catalysts in a temperature range from −60° C. to +200° C., preferably from 0° C. to +100° C. at normal pressure.

The halogenation is carried out in one of the abovementioned inert solvents, preferably in dimethylformamide, in a temperature range from −10° C. to +150° C., preferably from +25° C. to +80° C., at normal pressure.

The reactions not mentioned in detail for introducing the substituents R$^1$-R$^{15}$ such as, for example, acylations, nucleophilic or electrophilic substitutions, radical reactions, eliminations and rearrangements are carried out by methods known from the literature [cf. for example C. Ferri, Reaktionen der organischen Synthese (Reactions of Organic Synthesis), Georg Thieme Verlag, Stuttgart 1978 and J. March, Advanced Organic Chemistry, second edition, McGraw Hill Book Company].

The compounds of the general formulae (II), (IIa), (III), (IIIa) and (IV) are known per se or can be prepared by the customary method [Tietze and Eicher, Reaktionen und Synthesen organisch chemischen Praktikum (Reactions and Syntheses in Organic Chemical Practice), Georg Thieme Verlag, Stuttgart, New York, 1981; W. Fuerer, H. W. Gschwend, J. Org. Chem. 44, 1133–1136 (1979); F. W. Vierhapper, E. Trengler, K. Kratzl, Monatshefte für Chemie, 106, 1191–1201 (1975); John A. Elix and Vilas Jayanthi, Aust. J. Chem. 1987, 40 1841–1850].

The compounds of the formula (Ib) cannot be prepared according to the publication in Tetrahedron Letters, 45, pp. 3941–3947, (1974). However, it was possible to isolate them by customary methods by means of the new strain Penicillium funiculosum Thom [cf. Bodenwaschtechnik zur Isolierung von Boden- und Rhizosphärenpilzen, Methoden des mykologischen Laboratoriums (Soil washing technique for isolation of fungi which live in the soil and rhizosphere, Mycological Laboratory Methods), H. Kreisel, F. Schauer, Gustav Fischer Verlag, Stuttgart, New York, 1987]. A culture of this strain was deposited in the German Collection for Microorganisms in Braunschweig on 08.03.1989 under the number DSM 5249.

The compounds of the general formulae (V), (VI) and (VII) are known or can be prepared by known methods [for example J. March, "Advanced Organic Chemistry", Second edition].

The new and the known compounds of the formula (I) and (Ia) show an unforeseeable, useful spectrum of pharmacological action. They influence the release of ANP, the contractility of the heart, the tone of the smooth musculature and the electrolyte and fluid balance and act both partially or completely as digitalis antagonists or digitalis agonists.

They can therefore be employed in medicaments for the treatment of pathologically altered blood pressure or cardiac insufficiency, and as coronary therapeutics or as a therapeutic in digitalis poisoning.

Moreover, they can be employed for the treatment of cardiac arrhythmias, renal insufficiency, cirrhosis of the liver, ascites, lung oedema, cerebral oedema, oedema of pregnancy or glaucoma.

The antihypertensive action of 3-(1-hydroxy-3-methylbutyl)-4,11-dimethoxy-9-methyl-7H-dibenzo[b,g]-[1,5]dioxocin-5-one was investigated in rats with "reduced renal mass" hypertonia. The "reduced renal mass" (RRM) hypertonia was produced by 5/6 nephrectomy with administration of a 0.5% strength saline solution instead of drinking water based on the method described by von Hvart et al. (1983).

The compound from Example 39 acted in this form of hypertonia with an oral ED$_{20}$ (20% reduction of the systolic blood pressure on indirect measurement in conscious rats) of 100 mg/kg.

The compounds from Examples 12, 34, 74 and 76, for their part, stimulate ANP release by 292, 265, 196 and 192 percent in the isolated rat atrium. The ANP concentration in the bath fluid was determined radioimmunologically [J. P. Stasch, H. Grote, S. Kazda, C. Hirth, Dynorphin stimulates the release of ANP from isolated rat atria, Eur. J. Pharmacol. 159, 101 (1989)].

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, where, for example, in the case of the use of water as a diluent, if appropriate organic solvents can be used as auxiliary solvents.

Auxiliaries which may be mentioned are, for example: water, non-toxic organic solvents, such as paraffins (for example mineral oil fractions), vegetable oils (for example ground nut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates, arylsulphonates), detergents (for example lignin-sulphite waste liquors, methylcellulose, starch and polyvinylpyrrolidone) and lubricants (for example magnesium stearate, talc, stearic acid and sodium lauryl sulphate).

Administration is carried out in a customary manner, preferably orally or parenterally, in particular perlingually or intravenously. In the case of oral administration, in addition to the excipients mentioned, tablets may of course also contain additions, such as sodium citrate, calcium carbonate and dicalcium phosphate together with various additives, such as starch, preferably potato starch, gelatin and the like. Furthermore, lubricants, such as magnesium stearate, sodium lauryl sulphate and talc may additionally be used for tabletting. In the case of aqueous suspensions, various flavour enhancers or colorants may be added to the active compounds in addition to the abovementioned auxiliaries.

In the case of parenteral administration, solutions of the active compounds may be employed using suitable liquid excipient materials.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, in particular depending on the body weight or the type of application route, on individual behaviour toward the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of larger amounts, it may be advisable to divide these into a number of individual doses during the course of the day.

Preparation of starting compounds

EXAMPLE I

Methyl 5-formyl-2-[2-methoxy-6-(2-tetrahydropyranyloxymethyl)]-phenoxybenzoate

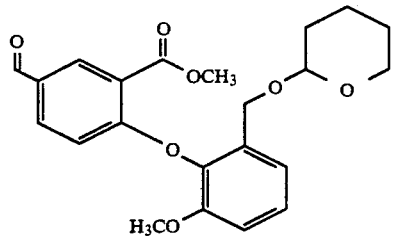

8.2 g (34.6 mmol) of 2-methoxy-6-(2-tetrahydropyranyloxymethyl)phenol, 5.3 g (38 mmol) of potassium carbonate and 3.0 g (38 mmol) of copper oxide are added to a solution of 10 g (34.6 mmol) of methyl 2-bromo-5-dimethoxymethyl-benzoate in 25 ml of absolute pyridine. The mixture is heated to 130° C.. After 3 h, a further 3.0 g (38 mmol) of copper oxide are added. After a reaction time of 12 h, the solvent is removed by distillation, the residue is taken up in dichloromethane and the mixture extracted with dilute hydrochloric acid. The organic phase is washed with water, dried over magnesium sulphate and evaporated in vacuo, and the residue is purified by column chromatography on silica gel using petroleum ether/ether 1:1.

Yield: 6.5 g (48% of theory)
MS: EI: 400, 315, 300, 255, 239
SF: $C_{22}H_{24}O_7$ (400)

EXAMPLE II

Methyl 5-formyl-2-[2-methoxy-4-methyl-6-(2-tetrahydropyranyloxymethyl)]-3-phenoxybenzoate

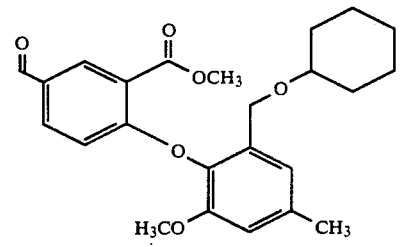

The title compound was prepared analogously to the procedure for Example I.
Yield: 78% of theory
MS: (EI): 414, 314, 269, 135
SF: $C_{23}H_{26}O_7$ (414)

EXAMPLE III

Methyl 5-formyl-2-(6-hydroxymethyl-2-methoxy)phenoxybenzoate

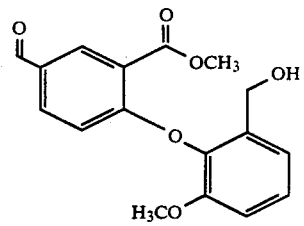

100 mg (0.25 mmol) of the compound from Example I are dissolved in a mixture of 2 of acetic acid, 1 ml of tetrahydrofuran and 0.5 ml of water and the mixture is heated to 50° C. for 4 h. After a further 12 h at room temperature, the mixture is concentrated in vacuo, and the residue is codistilled three times with toluene and purified by column chromatography on silica gel using petroleum ether/ethyl acetate 2:1.

Yield: 60.5 mg (76% of theory)
MS: (EI): 316, 255, 180, 148, 136
SF: $C_{17}H_{16}O_6$ (316)

The compounds shown in the following Table 1 are prepared analogously to the procedure for Example III:

TABLE 1

Structure: methyl 2-(6-methoxy-2-(hydroxymethyl)phenoxy)-5-R²-benzoate

| Ex. No. | R² | Formula (EI-electron impact) | SF* |
|---|---|---|---|
| IV | -CH(OH)-CH₂-CH(CH₃)₂ (with OH) | 374, 255, 239, 220, 205 | C₂₁H₂₆O₆ (374) |
| V | -CH(OH)-CH₂-CH₃ | 346, 285, 269, 255, 239 | C₁₉H₂₂O₆ (346) |
| VI | -CH(OH)-CH₂-CH₂-CH₃ | 360, 255, 239, 181 | C₂₀H₂₄O₆ (360) |
| VII | -CH(OH)-CH₂-C₆H₅ | 408, 317, 137 | C₂₄H₂₄O₆ (408) |
| VIII | -CH(OH)-C₆H₅ (with CH₃) | 394, 317, 269, 226 | C₂₃H₂₂O₆ (394) |
| IX | -CH(OH)(CH₃)-C₆H₄-Cl (4-Cl) | 428, 351, 179, 153 | C₂₃H₂₁ClO₆ (428) |
| X | -CH(OH)-CH₂-CH(CH₃)-CH₃ | 388, 181, 151 | C₂₂H₂₈O₆ (388) |

*SF = Summary Formula

EXAMPLE XI

5-Formyl-2-(6-hydroxymethyl-2-methoxy)phenoxybenzoic acid

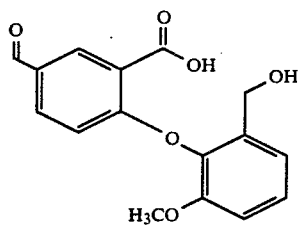

300 mg (0.95 mmol) of the compound from Example 3 are dissolved in 15 ml of tetrahydrofuran and 7.3 ml of a 0.2 N lithium hydroxide solution in water are added. After 16 h at 6° C., 6 ml of 32% strength hydrochloric acid are added to the solution. The substance crystallizes out. After 2 h, the precipitate is filtered off with suction, and the residue is washed with some water and dried over phosphorus pentoxide.

Yield: 192 mg (67% of theory)

MS: EI: 302, 166, 148, 136

SF: C₁₆H₁₄O₆ (302)

The compounds shown in the following Table 2 are prepared analogously to the procedure for Example XI:

TABLE 2

Structure: 2-(6-methoxy-2-(hydroxymethyl)-4-R⁶-phenoxy)-5-R²-benzoic acid

| Ex. No. | R² | R⁶ | Formula (EI) | SF |
|---|---|---|---|---|
| XII | -CH(OH)-CH₂-CH(CH₃)₂ | H | 360, 342, 255, 206, 167 | C₂₀H₂₄O₆ (360) |
| XIII | -CH(OH)-CH₂-CH₃ | H | 332, 167, 137 | C₁₈H₂₀O₆ (332) |
| XIV | -CH(OH)-CH₂-CH₂-CH₃ | H | 346, 167, 149, 137 | C₁₉H₂₂O₆ (346) |
| XV | -CH(OH)-CH₂-C₆H₅ | H | 394, 376, 303, 137 | C₂₃H₂₂O₆ (394) |
| XVI | -CH(OH)-C₆H₅ (with CH₃) | H | 380, 227, 137 | C₂₂H₂₀O₆ (380) |
| XVII | -CH(OH)(CH₃)-C₆H₄-Cl (4-Cl) | H | 414, 257, 223 | C₂₂H₁₉ClO₆ (414) |
| XVIII | -CH(OH)-CH₂-CH(CH₃)-CH₃ | CH₃ | 374, 356, 206, 188, 151 | C₂₁H₂₆O₆ (374) |

EXAMPLE XIX

Methyl 5-(1-hydroxy-3-methylbutyl)-2-[2-methoxy-4-methyl-6-(2-tetrahydropyranyloxymethyl)]-phenoxybenzoate The title compound is obtained analogously to the procedure for Example 140.

Yield: 50% of theory
MS (EI): 472, 327, 315, 285, 253
SF: $C_{27}H_{36}O_7$ (472)

The compounds shown in the following Table 2a were obtained analogously to the procedure for Example 140.

TABLE 2a

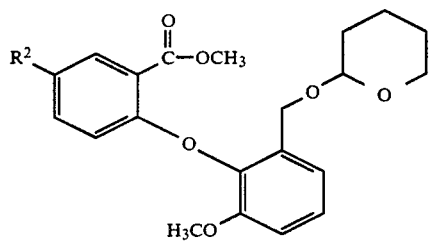

| Ex. No. | $R^2$ | Formula (EI) | SF |
|---|---|---|---|
| XX | OH, CH(CH$_3$)CH$_2$-CH(CH$_3$)CH$_3$ | 458, 313, 301, 239, 181 | $C_{26}H_{34}O_7$ (458) |
| XXI | OH, CH(CH$_3$)CH$_2$-CH$_3$ | 430, 344, 301, 285, 239 | $C_{24}H_{30}O_7$ (430) |
| XXII | OH, CH(CH$_3$)CH$_2$-CH$_2$-CH$_3$ | DCI: 462 (M + NH$_4$), 444, 427, 361, 343 | $C_{25}H_{32}O_7$ (444) |
| XXIII | OH, CH(CH$_3$)CH$_2$-phenyl | DCI: 493 (M + H$^+$), 409, 334, 316, 299 | $C_{29}H_{32}O_7$ (492) |
| XXIV | OH, CH(CH$_3$)-phenyl | 478, 393, 333, 239 | $C_{28}H_{30}O_7$ (478) |
| XXV | OH, CH(CH$_3$)-(4-Cl-phenyl) | 512, 394, 275 | $C_{28}H_{29}ClO_7$ (512) |

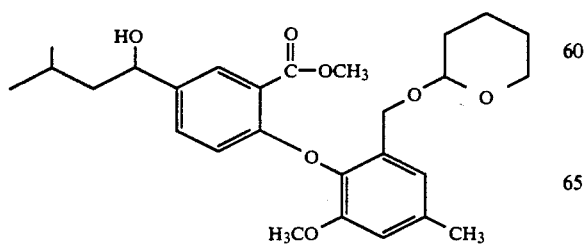

The compounds shown in Table 2b were prepared in analogy to the procedure of Example I:

TABLE 2b

[Structure: benzaldehyde with OCH₃, CO₂CH₃, and phenoxy group with R⁵, R, R⁷ substituents]

| Ex. No. | R⁵ | R⁷ | R | Formula (EI) | SF |
|---|---|---|---|---|---|
| XXVI | $-CH_2O$-(tetrahydropyranyl) | H | OCH₃ | 430, 330, 285, 269 | $C_{23}H_{26}O_8$ (430) |
| XXVII | $-CH_2O$-(tetrahydropyranyl) | CH₃ | H | 414, 269, 253, | $C_{23}H_{26}O_7$ (414) |
| XXVIII | $-CH_2O$-(tetrahydropyranyl) | Br | OCH₃ | 510, 508, 410, 408, 378 | $C_{23}H_{25}BrO_3$ (509) |
| XXIX | $-CH(OH)-CH_3$ | CH₃ | OCH₃ | 374, 324, 299, 256, 164 | $C_{20}H_{22}O_7$ (374) |

The compounds shown in Table 2c were prepared in analogy to the procedure of Example III:

TABLE 2c

[Structure: phenol with OH, OCH₃, CO₂CH₃, and phenoxy group with CH₂OH, R, R⁷ substituents]

| Ex. No. | R⁷ | R | Formula (EI) | SF |
|---|---|---|---|---|
| XXX | H | OCH₃ | 404, 347, 285, 269, 242 | $C_{22}H_{28}O_7$ (404) |
| XXXI | CH₃ | H | 398, 342 | $C_{22}H_{28}O_6$ (388) |

TABLE 2c-continued

[Structure similar with CH₂OH group]

| Ex. No. | R⁷ | R | Formula (EI) | SF |
|---|---|---|---|---|
| XXXII | Br | OCH₃ | 484, 482 | $C_{22}H_{27}BrO_7$ (483) |

The compounds shown in Table 2d were prepared in analogy to the procedure of Example 140.

TABLE 2d

[Structure with OH, OCH₃, CO₂CH₃, phenoxy with R⁵, R, R⁷]

| Ex. | R⁵ | R⁷ | R | Formula (EI) | SF |
|---|---|---|---|---|---|
| XXXIII | $-CH_2O$-(tetrahydropyranyl) | H | OCH₃ | 488, 347, 331, 299, 269 | $C_{27}H_{36}O_6$ (488) |

TABLE 2d-continued

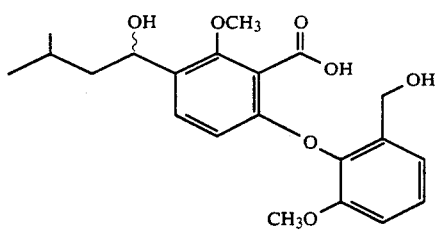

| Ex. | R⁵ | R⁷ | R | Formula (EI) | SF |
|---|---|---|---|---|---|
| XXXIV | —CH₂O—(tetrahydropyran) | CH₃ | H | 490, (M + NH₄)⁺, 455, 388, 371, 253 | $C_{27}H_{36}O_7$ (472) |
| XXXV | —CH₂O—(tetrahydropyran) | Br | OCH₃ | 568, 566, 425, 409, 349 | $C_{27}H_{35}BrO_8$ (567) |
| XXXVI | —CH(OH)—CH₃ | CH₃ | OCH₃ | 432, 375, 326, 297, 165 | $C_{24}H_{32}O_4$ (432) |

EXAMPLE XXXVII 5-(1-Hydroxy-3-methylbutyl)-2-(6-hydroxymethyl-2-methoxy)phenoxy-6-methoxy-benzoic acid 105 mg (0.26 mmol) of the compound from Example XXX are dissolved in 2 ml of methanol and 145 mg (2.6 mmol) of KOH are added. After 12 h at room temperature, the batch is concentrated in vacuo, the residue is taken up in water and the mixture is acidified with dilute hydrochloric acid. The aqueous phase is extracted using CH₂Cl₂, and the combined organic phases are dried over MgSO₄ and concentrated in vacuo. The substance thus obtained is processed further without characterization.

The compounds shown in Table 2e were prepared in analogy to the procedure of Example XXXVII:

TABLE 2e

| Ex. No. | R⁵ | R⁷ | R | Formula (EI) | SF |
|---|---|---|---|---|---|
| XXXVIII | —CH₂OH | CH₃ | H | 374 | $C_{21}H_{26}O_6$ (374) |
| XXXIX | —CH₂OH | Br | OCH₃ | 469 | $C_{21}H_{25}BrO_7$ (469) |
| XL | —CH(OH)—CH₃ | CH₃ | OCH₃ | 418 | $C_{23}H_{30}O_7$ (418) |

Exemplary embodiments

Example 1

3-Formyl-11-methoxy-7H-dibenzo[b,g][1,5]-dioxocin-5-one

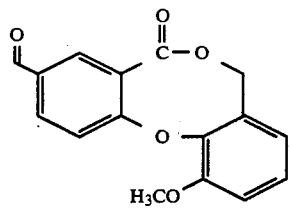

A solution of 180 mg (0.6 mmol) of the compound from Example XI and 663 μl (4.8 mmol) of triethylamine in 40 ml of absolute acetonitrile is added dropwise at 80° C. to a solution of 609 mg (2.4 mmol) of 2-chloro-1-methylpyridinium iodide in 40 ml of absolute acetonitrile over a period of 6 h. After a further hour at 80° C., the mixture is concentrated in vacuo, the residue is taken up in dichloromethane, and the solution is washed with water, dried over magnesium sulphate and concentrated. Purification is carried out by column chromatography on silica gel using petroleum ether/ethyl acetate 4:1. In the course of the separation, the eluent is changed to petroleum ether/ethyl acetate 1:2.

Yield: 73 mg (43% of theory)
MS: EI: 284, 239, 136
SF: $C_{16}H_{12}O_5$ (284)

The compounds shown in the following Table 3 were prepared analogously to the procedure for Example 1.

TABLE 3

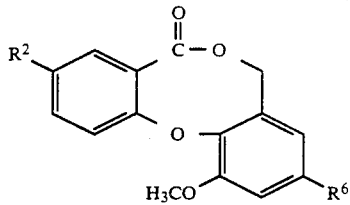

| Ex. No. | $R^2$ | $R^6$ | Formula (EI) | SF |
|---|---|---|---|---|
| 2 | OH–CH(CH(CH$_3$)$_2$) (1-hydroxy-3-methylbutyl) | H | 342, 285, 149, 137, | $C_{20}H_{22}O_5$ (342) |
| 3 | OH–CH–CH$_3$ | H | 314, 285, 149, 137 | $C_{18}H_{18}O_5$ (314) |
| 4 | OH–CH–CH$_2$CH$_3$ | H | 328, 285, 149, 137 | $C_{19}H_{20}O_5$ (328) |
| 5 | OH–CH–CH$_2$–Ph | H | 376, 285, 149, 137 | $C_{23}H_{20}O_5$ (376) |
| 6 | OH–CH(Ph) | H | 362, 283, 227, 213 | $C_{22}H_{18}O_5$ (362) |
| 7 | OH–CH(4-ClPh) | H | 396, 282, 139 | $C_{22}H_{17}ClO_5$ (396) |

TABLE 3-continued

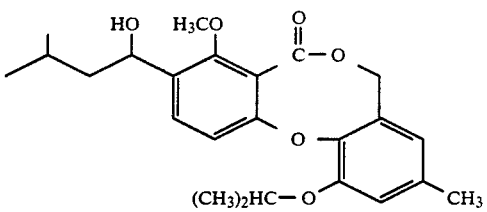

| Ex. No. | $R^2$ | $R^6$ | Formula (EI) | SF |
|---|---|---|---|---|
| 8 | OH–CH–CH$_2$–CH(CH$_3$)$_2$ | CH$_3$ | 356, 299, 151 | $C_{21}H_{24}O_5$ (356) |

Example 9

3-(1-Hydroxy-3-methylbutyl)-11-(1-methyl-ethoxy)-4-methoxy-9-methyl-7H-dibenzo[b,g][1,5]dioxocin-5-one

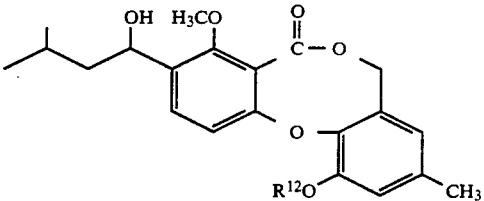

200 mg (0.54 mmol) of penicillide (Ib) in 2 ml of dimethylformamide are stirred under argon at 25° C. for 12 h with 0.5 ml (50 mmol) of isopropyl iodide and 160 mg (1.14 mmol) of anhydrous potassium carbonate. After evaporating in vacuo, the residue is taken up with 1 N aqueous hydrochloric acid and the mixture is exhaustively extracted with diethyl ether. After drying the organic phase, the evaporation residue is chromatographed on silica using petroleum ether/ether = 1/1. Fractions which are pure by thin layer chromatography are combined and evaporated.

Yield: 169 mg (72% of theory) of colourless solid
MS (EI): 414, 357, 315, 297, 269, 243, 219
SF: $C_{24}H_{30}O_6$ (414)

The compounds shown in the following Tables 4, 5, 6 and 7 are prepared analogously to the procedure for Example 9.

TABLE 4

| Ex. No. | $R^{12}$ | Formula (EI) | SF |
|---|---|---|---|
| 10 | –(CH$_2$)$_4$–Br | 508, 506, 490, 488, 451, 449, 269, 137, 135 | $C_{25}H_{31}BrO_6$ (507) |

TABLE 4-continued

[Structure: A compound with OH, H₃CO, isobutyl group, ester linkage C(=O)-O-CH₂- connected to aromatic ring with CH₃ and OR¹² substituents]

| Ex. No. | R¹² | Formula (EI) | SF |
|---|---|---|---|
| 11 | -CH₂-C(=O)-O-C(CH₃)₃ | DCI: 504, 486, 469, 448, 413 | $C_{27}H_{34}O_8$ (486) |
| 12 | -CH₂-C(=O)-OCH₂CH₃ | 458, 401, 283, 255 | $C_{25}H_{30}O_8$ (458) |
| 13 | -CH₂-C(=O)-NH₂ | 429, 372, 326, 297, 274 | $C_{23}H_{27}NO_7$ (429) |
| 14 | -CH₂-CH(CH₃)₂ | 428, 371, 269, 243 | $C_{25}H_{32}O_6$ (428) |
| 15 | -CH₂-CH₂-C₆H₅ | 476, 419, 401, 105 | $C_{29}H_{32}O_6$ (476) |
| 16 | -CH₂-C₆H₅ | 462, 405, 91 | $C_{28}H_{30}O_6$ (462) |
| 17 | -CH₂-C₆H₄-OCH₃ (para) | 492, 354, 315, 269 | $C_{29}H_{32}O_7$ (492) |
| 18 | -(CH₂)₅-CH₃ | 456, 399, 369, 353, 269 | $C_{27}H_{36}O_6$ (456) |
| 19 | -(CH₂)₂-CH(CH₃)₂ | 442, 385, 357, 339 | $C_{26}H_{34}O_6$ (442) |
| 20 | -CH₂-CH=CH₂ | 412, 355, 309 | $C_{24}H_{28}O_6$ (412) |
| 21 | -CH₂-CH₂-CH₃ | 414, 357, 329, 311 | $C_{24}H_{30}O_6$ (414) |
| 22 | -CH₂-cyclopropyl | 426, 369, 269, 179 | $C_{25}H_{30}O_6$ (426) |
| 23 | -CH₂-CH₃ | 400, 343, 313, 297 | $C_{23}H_{28}O_6$ (400) |
| 24 | -CH₂-(epoxide) | 428, 371, 341, 335 | $C_{24}H_{28}O_7$ (428) |
| 25 | -CH₂-CH=CH-C₆H₅ | 488, 431, 413 | $C_{30}H_{32}O_6$ (488) |

TABLE 4-continued
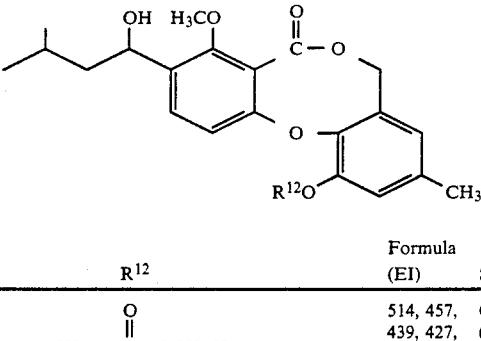
| Ex. No. | R[12] | Formula (EI) | SF |
|---|---|---|---|
| 26 | —(CH$_2$)$_5$—C(=O)—OCH$_2$CH$_3$ | 514, 457, 439, 427, 297 | C$_{29}$H$_{38}$O$_8$ (514) |
| 27 | —(CH$_2$)$_6$—OH | 472, 397, 369, 297 | C$_{27}$H$_{36}$O$_7$ (472) |
| 28 | —(CH$_2$)$_3$—OH | 430, 373, 355, 343, 337 | C$_{24}$H$_{30}$O$_7$ (430) |
| 29 |  | 440, 383, 315, 269 | C$_{26}$H$_{32}$O$_6$ (440) |
| 30 | 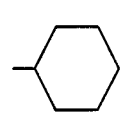 | 454, 315, 269, 243, 219 | C$_{27}$H$_{34}$O$_6$ (454) |
| 31 | 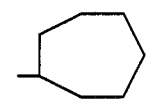 | 468, 411, 315, 269 | C$_{28}$H$_{36}$O$_6$ (468) |
| 32 | —CH$_2$—CH(O—C(CH$_3$)$_2$—O)—CH$_2$ | 486, 471, 429, 353, 341, 115 | C$_{27}$H$_{34}$O$_8$ (486) |
| 33 | 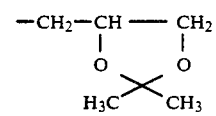 | FAB: 614, 597, 269 | C$_{33}$H$_{42}$O$_{11}$ (614) |
| 34 | 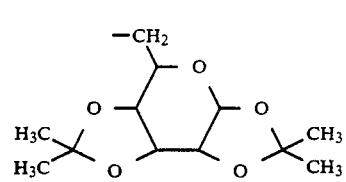 | DCI: 556, 538, 462, 444, 427 | C$_{30}$H$_{37}$NO$_9$ (555) |
| 35 | —CH$_2$—CH=CH—CH$_3$ | 426, 372, 315, 269 | C$_{25}$H$_{30}$O$_6$ (426) |
DCI*: Desorption Oericae ionization

TABLE 5

| Ex. No. | R¹²/R¹²' | Formula (EI) | SF |
|---|---|---|---|
| 36 | R¹² = R¹²' = —CH₂—(phenyl) | DCI: 445, 354, 298 | $C_{35}H_{36}O_6$ (552) |
| 37 | R¹² = —CH(phenyl)(phenyl); R¹²' = H | 538, 400, 252, 168 | $C_{34}H_{34}O_6$ (538) |
| 38 | R¹²' = H; R¹² = —CH₂O(CH₂)₂OCH₃ | 460, 354, 89 | $C_{25}H_{32}O_8$ (460) |

FAB**: Fast atom bombardment

TABLE 6

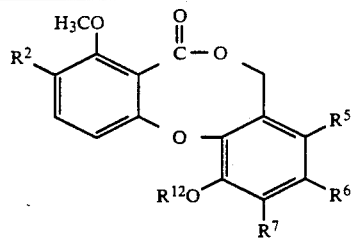

| Ex. No. | R² | R⁵ | R⁶ | R⁷ | R¹² | Formula (EI) | SF |
|---|---|---|---|---|---|---|---|
| 39 | (isobutyl-CH(OH)—) | Br | CH₃ | H | CH₃ | 466, 464 409, 407 363, 361, 322, 320 | $C_{22}H_{25}BrO_6$ (465) |
| 40 | (isobutyl-CH(OH)—) | H | CH₃ | Br | CH₃ | 466, 464, 409, 407 362, 360 | $C_{21}H_{25}BrO_6$ (465) |
| 41 | (isobutyl-CH(OH)—) | Br | CH₃ | Br | CH₃ | 546, 544, 542, 489, 487, 485, 443, 441, 439 | $C_{22}H_{24}Br_2O_6$ (544) |
| 42 | (isobutyl-CH=CH—) | H | CH₃ | H | H | 354, 343, 269, 163 | $C_{21}H_{22}O_5$ (354) |
| 43 | (isobutyl-CH(OH)—) | H | CH₃ | H | CH₂CH=CHCH₃ | 426, 369 | $C_{25}H_{30}O_6$ (426) |

TABLE 7

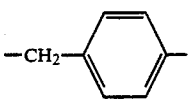

| Ex. No. | R¹² | Formula (EI) | SF |
|---|---|---|---|
| 44 | —CH₂—(epoxide) | 428, 371, 297, 269 | $C_{24}H_{28}O_7$ (428) |
| 45 | —CH₂—CH₂—OH | 416, 209 151 | $C_{23}H_{28}O_7$ (416) |

TABLE 8

| Ex. No. | R¹² | Formula (EI) | SF |
|---|---|---|---|
| 46 | —CH₂—(C₆H₄)—OCH₃ | FAB: 491 (M + H⁺) 154, 121 | $C_{29}H_{30}O_7$ (490) |

TABLE 8-continued

Structure (common to examples 47-63):

A compound with R¹²O substituent on the dibenzodioxocinone scaffold with H₃CO and CH₃ groups.

| Ex. No. | R¹² | Formula (EI) | SF |
|---|---|---|---|
| 47 | cyclopentyl | 438, 370 150 | $C_{26}H_{30}O_6$ (438) |
| 48 | $-CH_2-$(oxirane) | 426, 369, 151, 132 | $C_{24}H_{26}O_7$ (426) |
| 49 | $-CH_2-CH_2-Br$ | 478, 476, 420, 418, 353 | $C_{23}H_{25}BrO_6$ |
| 50 | $-CH(CH_3)_2$ | 412, 370 150 | $C_{24}H_{28}O_6$ (412) |
| 51 | $-CH_2-CH_3$ | 398, 341, 312, 297 151 | $C_{23}H_{26}O_6$ (398) |
| 52 | $-CH_2-$phenyl | 460, 403, 384, 354, 327 | $C_{28}H_{28}O_6$ (460) |
| 53 | $-CH_2-CH=CH_2$ | 410, 297, 240, 177 | $C_{24}H_{26}O_6$ (410) |
| 54 | $-CH_2-$cyclopropyl | 424, 297, 283, 269 | $C_{25}H_{28}O_6$ (424) |
| 55 | $-CH_2-C(=O)-C(CH_3)_3$ | 484, 428, 384, 327, 177 | $C_{27}H_{32}O_8$ (484) |
| 56 | $-CH_2-CH_2-CH_3$ | 412, 312, 297, 151 | $C_{24}H_{28}O_6$ (412) |
| 57 | $-CH_2-CH_2-$phenyl | 474, 432, 417, 370, 150 | $C_{29}H_{30}O_6$ (474) |
| 58 | $-CH-(C_6H_5)_2$ | DCI: 554 (M + NH₄⁺) 537, 453, 371, 167 | $C_{34}H_{32}O_6$ (536) |
| 59 | $-CH_2-CH(CH_3)_2$ | 426, 370, 297, 151 | $C_{25}H_{30}O_6$ (426) |
| 60 | $-(CH_2)_4-Br$ | 506, 504, 297, 177 | $C_{25}H_{29}O_6Br$ |
| 61 | $-S(=O)_2-CH_3$ | 448, 391, 283, 151 | $C_{22}H_{24}O_8S$ (448) |
| 62 | $-CH_2-C(=O)-NH_2$ | 427, 370, 312, 295, 269 | $C_{23}H_{25}NO_7$ (447) |
| 63 | $-CH_2-CH(CH_3)-O-C(CH_3)_2-O-$ (dioxolane) | 484, 469, 370, 353, 269 | $C_{27}H_{32}O_8$ (484) |

Example 64

3-(1-Acetoxy-3-methylbutyl)-11-methyl-7H-dibenzo[b,g][1,5]dioxocin-5-one

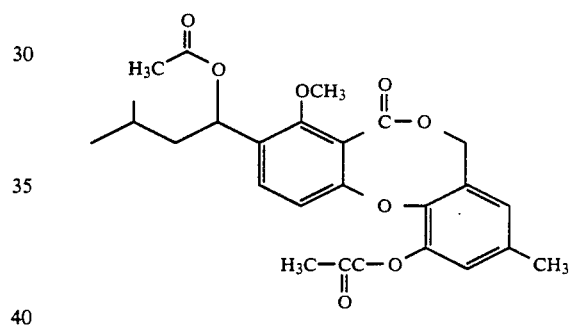

100 mg (0.27 mmol) of penicillide (Ib) are stirred in 2 ml of pyridine and 1 ml of acetic anhydride for 14 h at 25° C. with the exclusion of moisture. The reaction mixture is evaporated in vacuo, the residue is taken up in methylene chloride and the solution is washed with water. The evaporation residue of the dried organic phase is chromatographed on silica gel using hexane/diethyl ether.

Yield: 61 mg (50% of theory) of colorless solid
MS (EI): 456, 414, 354, 315, 298, 285, 269, 219
SF: $C_{25}H_{28}O_8$ (456)

Example 65

11-Hydroxy-4-methoxy-9-methyl-3-(3-methylbutan-1-onyl)-7H-dibenzo[b,g][1,5]dioxocin-5-one

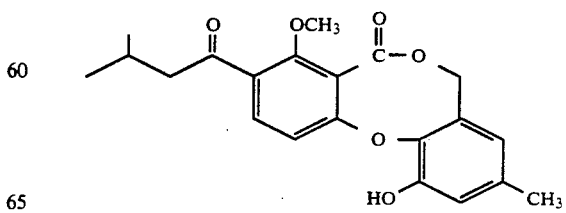

800 mg (2.2 mmol) of penicillide (Ib) are stirred at 25° C. under argon for 3 h in 15 ml of methylene chloride and 880 mg (4.1 mmol) of pyridinium chlorochromate. After addition of 200 ml of diethyl ether, the mixture is filtered through silica gel Si60. The evaporation residue of the filtrate is chromatographed on silica gel using petroleum ether/ether =1:1

Yield: 363 mg (45% of theory) of colorless solid
MS (EI): 370, 313, 177
SF: $C_{21}H_{22}O_6$ (370)

The compounds shown in the following Table 9 were prepared analogously to the procedure for Example 65:

evaporated. Chromatography of the residue on silica gel Si60 in petroleum ether/ether =2:1 with fractionated elution yields 65 mg (53% of theory) of colorless solid.

MS: EI: 456, 372, 354, 315, 269
Structural formula: $C_{26}H_{32}O_7$ (456)

Example 71

4,11-Dimethoxy-9-methyl-3-(1-hydroximino-3-methylbutyl-7H-dibenzo[b,g][1,5]dioxocin-5-one

TABLE 9

| Ex. No. | $R^1$ | $R^2$ | $R^7$ | $R^{12}$ | Formula (EI) | SF |
|---|---|---|---|---|---|---|
| 66 | OCH₃ | (isobutyl ketone) | H | —CH₂—CH₃ | 398, 341, 177 | $C_{23}H_{26}O_6$ (398) |
| 67 | OCH₃ | (isobutyl ketone) | H | —CH₂—CH(CH₃)₂ | 426, 335, 169, 150 | $C_{25}H_{30}O_6$ (426) |
| 68 | OCH₃ | (isobutyl with OH) | OH | CH₃ (with OH) | 430, 373 | $C_{24}H_{30}O_7$ (430) |
| 69 | —O—(CH₂)₂—N(C₂H₅)₂ | (isobutyl with OH) | H | CH₃ | 471, 414 | $C_{27}H_{37}NO_6$ (471) |

Example 70

11-Hydroxy-4-methoxy-9-methyl-3-(1-(tetrahydropyranyl-2-oxy)-3-methylbutyl)-7H-dibenzo[b,g][1,5]dioxocin-5-one

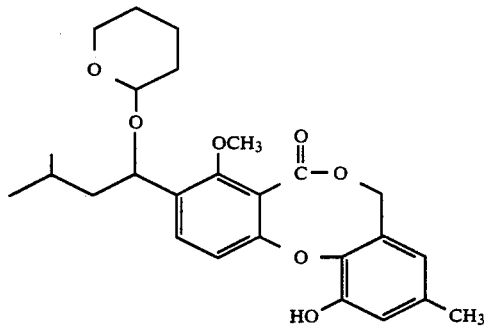

100 mg (0.27 mmol) of penicillide (Ib) in 1 ml of absolute methylene chloride are stirred at 25° C. for 12 h with 72 μl (0.8 mmol) of dihydropyran and catalytic amounts of p-toluene sulphonic acid. After addition of 10 ml of methylene chloride, the mixture is washed with aqueous bicarbonate, washed until neutral, dried and

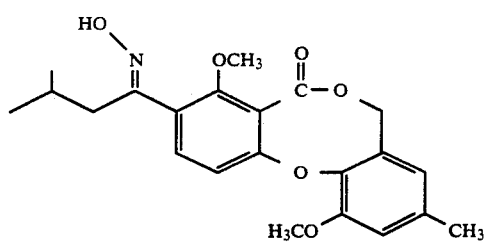

100 mg (0.26 mmol) of 4,11-dimethoxy-9-methyl-3-(1-oxo-3-methylbutyl)-7H-dibenzo[b,g][1,5]dioxocin-5-one are stirred at 25° C. for 60 h in 3 ml of glacial acetic acid, 36 mg (0.52 mmol) of hydroxylamine hydrochloride and 43 mg (0.52 mmol) of sodium acetate. After evaporating in a high vacuum, the residue is taken up in methylene chloride, the solution is washed with water and dried, and the evaporation residue is chromatographed on silica gel Si60 in ether/petroleum ether =2:1.

Yield: 40 mg (39% of theory) of colorless solid
MS: EI: 399, 367, 325
Structural formula: $C_{22}H_{25}NO_6$ (399)

Example 72

3-(1-Azido-3-methylbutyl)-11-hydroxy-4-methoxy-9-methyl-7H-dibenzo[b,g][1,5]dioxocin-5-one

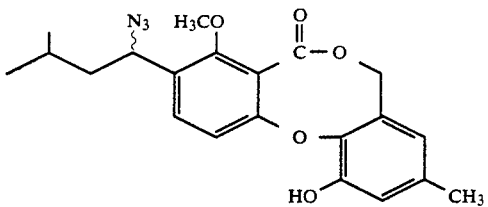

4.6 g (17.6 mmol) of triphenylphosphine and 29.3 ml of a freshly prepared 0.6 N solution of hydrazoic acid in toluene are added to 6 g (16.1 mmol) of penicillide (1b) in 100 ml of tetrahydrofuran. 2.7 ml (17.6 mmol) of diethyl azodicarboxylate are added dropwise to this mixture at 0° C. under argon. The mixture is then stirred at 25° C. for 12 h. After diluting with methylene chloride, the mixture is washed with aqueous bicarbonate, dried and evaporated. Chromatography on silica gel Si60 in diethyl ether/petroleum ether =2:1 yields 5.6 g (88% of theory) of colorless solid.
MS (EI): 397, 355, 299, 176, 163
SF: $C_{21}H_{23}N_3O_5$ (397)

Example 73

3-(1-Azido-3-methylbutyl)-4,11-dimethoxy-9-methyl-7H-dibenzo[b,g][1,5]dioxocin-5-one

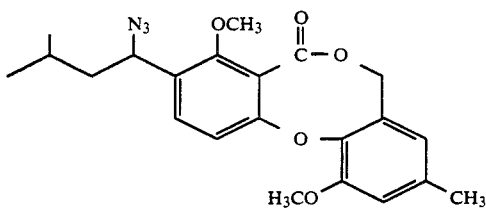

The title compound was prepared analogously to the procedure for Example 72.
MS (EI): 411, 369, 314, 383, 163
SF: $C_{22}H_{25}N_3O_5$ (411)

Example 74

3-(1-Amino-3-methylbutyl)-11-hydroxy-4-methoxy-9-methyl-7H-dibenzo[b,g][1,5]dioxocin-5-one

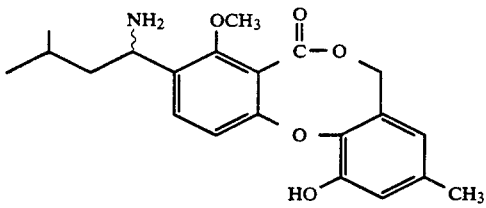

63.3 ml of a solution of 20 g of boric acid and 20 g of nickel dichloride hexahydrate in 500 ml of ethanol are added to 5.63 g (14 mmol) of the compound from Example 72. 1.1 g (28.4 mmol) of sodium borohydride in 20 ml of ethanol are rapidly added dropwise to this mixture. After stirring at 25° C. for 12 h, the mixture is evaporated in vacuo, the residue is taken up with methylene chloride and the solution is washed with water. After drying and evaporating, the residue is purified by chromatography on silica gel Si60 in methylene chloride/methanol/concentrated aqueous ammonia=200:10:1.
Yield: 3.9 g (76% of theory) of colorless solid.
MS (DCI) 372, 355
SF: $C_{21}H_{25}NO_5$ (371)

Example 75

3-(1-Amino-3-methylbutyl)-4,11-dimethoxy-9-methyl-7H-dobenzo[b,g][1,5-9 dioxocin-5-one

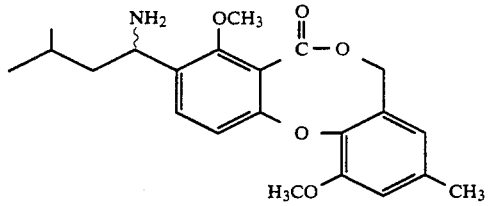

The compound was prepared analogously to the procedure for Example 74.
MS (FAB): 386, 369, 355
SF: $C_{22}H_{27}NO_5$ (385)

Example 76

11-(4-Diethylaminobutyloxy-3-(1-hydroxy-3-methylbutyl)-4-methoxy-9-methyl-7H-dibenzo[b,g][1,5]dioxocin-5-one

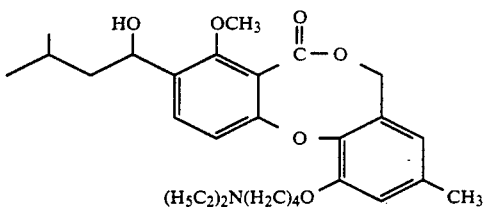

118 mg (0.23 mmol) of the compound from Example 10 are stirred at 70° C. under argon for 12 h with 1 ml of dimethylformamide, 48 μl (0.46 mmol) of diethylamine and catalytic amounts of sodium iodide. After evaporating in a high vacuum, the residue is taken up in methylene chloride, and the solution is washed with water, dried and evaporated. Chromatography on silica gel Si60 in methylene chloride/methanol/concentrated aqueous ammonia yields 86 mg (74% of theory) of colorless solid.
MS (DCI): 500, 484
SF: $C_{29}H_{41}NO_6$ (499)

Example 77

3-(1Hydroxy-3-methylbutyl)-4-methoxy-9-methyl-11-methylsulphonyloxy-7H-dibenzo[b,g][1,5]dioxocin-5-one

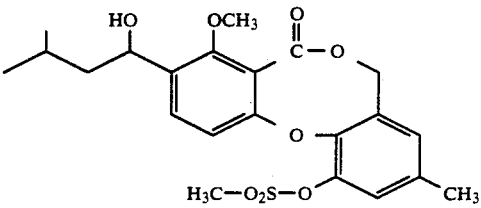

0.14 ml (1.0 mmol) of triethylamine and 86 μl (1.1 mmol) of methanesulphonyl chloride are added at 0° C. under argon to 150 mg (0.4 mmol) of penicillide (Ib) in 3 ml of methylene chloride and the mixture is stirred at 25° C. for 12 h. Acidifying to pH 2, extracting with methylene chloride, washing, drying and evaporating yields, after chromatography on silica gel Si60 in ether/petroleum ether 2:1, 75 mg (41% of theory) of colorless solid

MS (EI): 450, 393, 365, 347
SF: $C_{22}H_{26}O_8S$ (450)

Example 78

4,11 Dimethoxy-3-(1-hydroxypropyl)-9-methyl-7H-dibenzo-[b,g][1,5]dioxocin-5-one

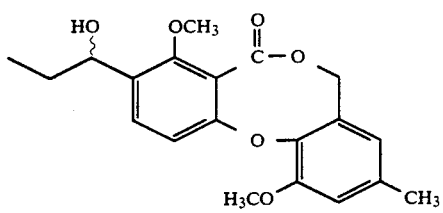

0.7 ml (1.4 mmol) of a 2 M ethylmagnesium bromide solution in tetrahydrofuran are added under argon at 0° C. to 53 mg (0.15 mmol) of the compound from Example 101 in 4 ml of absolute tetrahydrofuran and the mixture is stirred at 25° C. for 1 h. After addition of 2 ml of 1 N hydrochloric acid, the mixture is diluted with methylene chloride, washed with water, dried and evaporated. After chromatographic purification on silica gel Si60 (petroleum ether/ether gradient), 36 mg of the main product (62% of theory) is obtained as a colorless solid.

MS (EI): 358, 329, 311, 299, 283, 242
SF: $C_{25}H_{32}O_8$ (358)

The compounds shown in Table 10 were prepared analogously to the procedure for Example 78.

TABLE 10

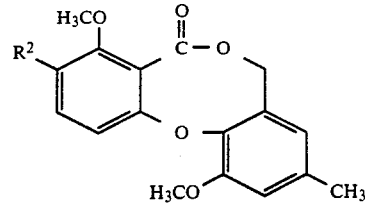

| Ex. No. | $R^2$ | Formula (EI) | SF |
|---|---|---|---|
| 79 | OH, C(CH₃)₃ | 386, 329, 311, 299, 283, 242 | $C_{22}H_{26}O_6$ (386) |
| 80 | OH, C(CH₃)₂ | 372, 329, 311, 299, 283 | $C_{21}H_{24}O_6$ (372) |
| 81 | OH, CH₃ | 344, 283 | $C_{19}H_{20}O_6$ (344) |
| 82 | OH, CH=CH₂ | 356, | $C_{20}H_{20}O_6$ (356) |
| 83 | OH, (CH₂)₅—CH₃ | 414, 329, 283, 242 | $C_{24}H_{30}O_6$ (414) |
| 84 | OH, phenyl | 406, 325, 262 | $C_{24}H_{22}O_6$ (406) |
| 85 | OH, (CH₂)₂—CH₃ | 372, 329, 311, 299, 283, 242 | $C_{21}H_{24}O_6$ (372) |
| 86 | OH, CH—CH₂—CH₃, CH₃ | 386, 311, 299, 283, 242 | $C_{22}H_{26}O_6$ (386) |
| 87 | OH, cyclohexyl | 412, 329, 283 | $C_{24}H_{28}O_6$ (412) |
| 88 | OH, 4-chlorophenyl | 440, 283, 167 | $C_{24}H_{21}ClO_6$ (440.5) |
| 89 | OH, (CH₂)₂—CH=CH₂ | 384, 329, 283, 242, | $C_{22}H_{24}O_6$ (384) |
| 90 | OH, 4-fluorophenyl | 424, 135, 123, 109 | $C_{24}H_{21}O_6F$ (424) |
| 91 | HO, 2,4,6-trimethylphenyl | 448, 399, 301, 271, 242 | $C_{27}H_{28}O_6$ (448) |
| 92 | HO, 2-methylphenyl | 420, 402, 269, 119, 44 | $C_{25}H_{24}O_5$ (420) |

TABLE 10-continued

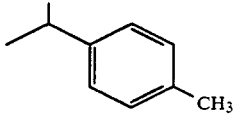

| Ex. No. | $R^2$ | Formula (EI) | SF |
|---|---|---|---|
| 93 | HO-CH(CH₃)-C₆H₄-CH₃ | 420, 402, 143, 119 | $C_{25}H_{24}O_6$ (420) |

EXAMPLE 94

3-(1-Chloro-3-methylbutyl)-11-hydroxy-4-methoxy-9-methyl-7H-dibenzo[b,g][1,5]dioxocin-5-one

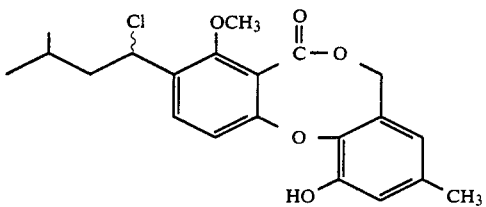

200 mg (0.54 mmol) of penicillide (Ib) are heated under reflux for 5 h (exclusion of moisture) in 1 ml of dioxane and 0.38 ml (5.2 mmol) of thionyl chloride. After evaporating in vacuo, the residue is taken up in methylene chloride, and the solution is washed with aqueous bicarbonate, then with water, dried and evaporated. Chromatography on silica gel Si60 in ether/petroleum ether=2:1 yields 187 mg (93% of theory) of colorless solid.

$^1$H-NMR (CDCl₃): δ=7.63 (1H, d); 6.91 (1H, d); 6.87 (1H, d); 6.40 (1H, d); 6.09 (1H, s); 5.40 (1H, mc); 5.09 (1H, mc); 4.03 (3H, s); 2.26 (3H, s); 2.05 (1H, mc); 1.75 (2H, mc); 0.95 (6H, d).

SF: $C_{21}H_{23}ClO_5$ (390.4)

EXAMPLE 95

3-(1-Chloro-3-methylbutyl)-4,11-dimethoxy-9-methyl-7H-dibenzo[b,g][1,5]dioxocin-5-one

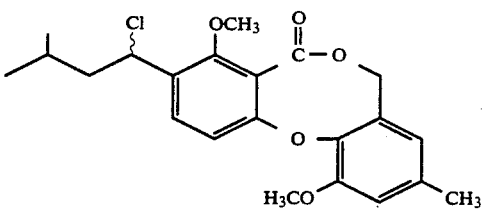

The title compound was prepared analogously to the procedure for Example 94.
MS (EI): 406, 404, 313, 163
SF: $C_{22}H_{25}ClO_5$ (404.4)

EXAMPLE 96

4,11-Dimethoxy-9-methyl-3-(3-methylbutyl)-7H-dibenzo[b,g][1,5]dioxocin-5-one

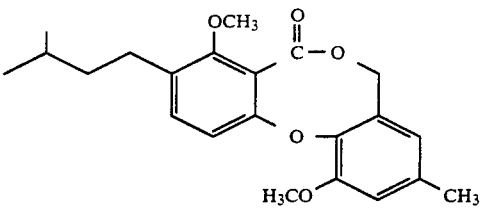

The title compound was prepared analogously to the procedure for Example 97.
MS (EI): 370, 342, 325, 313, 299
SF: $C_{22}H_{26}O_5$ (370)

EXAMPLE 97

11-Hydroxy-4-methoxy-9-methyl-3-(3-methylbutyl)-7H-dibenzo[b,g][1,5]dioxocin-5-one

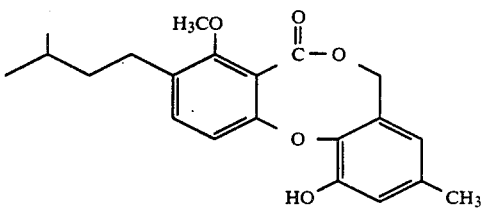

131 mg (0.3 mmol) of the compound from Example 94 in 2.5 ml of toluene and 200 μl (0.74 mmol) of tributyltin hydride are heated under reflux. After addition of 29 mg (0.18 mmol) of 2,2'-azodiisobutyronitrile, the mixture is heated under reflux for a further 2 h and evaporated in vacuo, and the residue is purified by chromatography on silica gel Si60 using petroleum ether/ether=5:1.

Yield: 128 mg (90% of theory) of colorless crystals from diethyl ether
MS (EI):=356,299,220,163
SF: $C_{21}H_{24}O_5$ (356)

EXAMPLE 98

4,11-Dimethoxy-9-methyl-3-(-3-methyl-1-butenyl)-7H-dibenzo[b,g][1,5]dioxocin-5-one

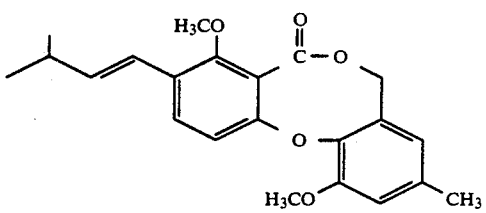

1.1 g (3.0 mmol) of the compound from Example 95 in 10 ml of dimethylformamide, 2.2 ml (15.3 mmol) of 7-methyl-1,5,7-triazabicyclo[4.4.0]dec-5-ene and 0.65 g of copper(I) oxide are stirred at 80° C. for 12 h in an argon atmosphere. After filtering, the mixture is evaporated in vacuo, the residue is taken up with methylene chloride, 1N aqueous hydrochloric acid is added, then the mixture is washed with water, dried and evaporated. Chromatography on silica gel Si60 in petroleum ether/ether=3:1 yields 730 mg (65% of theory) of glassy solid.

MS (EI): 368, 353, 335, 323, 218, 203
SF: C22H25O5 (368)

EXAMPLE 99

11-Hydroxy-4-methoxy-9-methyl-3-(1-N-((S)-2-pyrrolidone-5-carboxamido)-3-methylbutyl)-7H-dibenzo[b,g][1,5]dioxocin-5-one

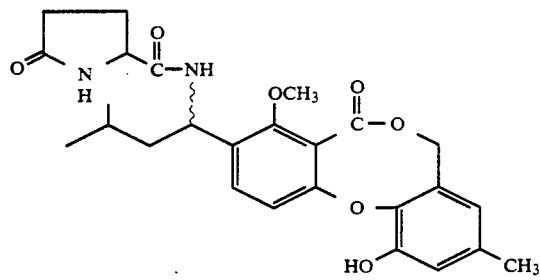

85 μl (0.49 mmol) of diisopropylethylamine in 1 ml of dimethylformamide are added at −55° C. under argon to 63 mg (0.49 mmol) of (S)-2-pyrrolidone-5-carboxylic acid. After addition of 38 μl (0.54 mmol) of methanesulphonyl chloride, the mixture is stirred at −55° C. for 30 minutes. 166 μl (1.2 mmol) of triethylamine and 0.2 g (0.54 mmol) of the compound from Example 74 in 1 ml of dimethylformamide are then added dropwise. After stirring at 25° C. for 30 minutes, the mixture is diluted with methylene chloride and washed at pH 3-4 with water, dried and evaporated. Chromatography on silica gel Si60 in methylene chloride/methanol 20:1 gives 92 mg (35% of theory) of colorless solid.

MS (DCI): 483, 425, 220, 186
SF: C26H30N2O7 (482)

EXAMPLE 100

4,11-Dimethoxy-3-(1,2-epoxy-3-methylbutyl)-9-methyl-7H-dibenzo[b,g][1,5]dioxocin-5-one

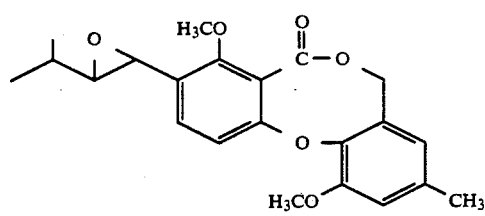

43 mg (0.12 mmol) of the compound from Example 98 in 2 ml of dichloromethane are stirred at 25° C. for 3 h with an excess of meta-chloroperbenzoic acid. After washing with aqueous bicarbonate, drying and evaporating, the residue is chromatographed on silica gel Si60 in petroleum ether/ether 1:1. 12 mg (27% of theory) of colorless solid are obtained in the main fraction.

MS (EI): 384, 267, 239, 234, 219, 191
SF: C22H24O6 (384)

EXAMPLE 101

4,11-Dimethoxy-9-methyl-3-oxoformylene-7H-dibenzo[b,g][1,5]dioxocin-5-one

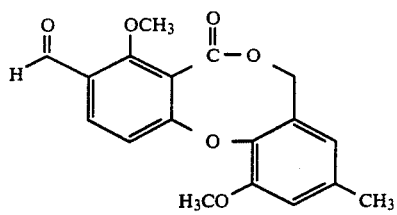

An ozone/oxygen mixture is introduced at −60° C. until saturation into 5.6 g (15.2 mmol) of the compound from Example 98 in 100 ml of methylene chloride and 10 ml of methanol in a standard apparatus [Organikum, 9th edition, page 298 ff., VEB Deutscher Verlag der Wissenschaften]. After addition of 19 ml of tributylphosphine, the mixture is warmed to 25° C. with stirring, washed with hexane and chromatographed on silica Si60 in ether/petroleum ether 1:1.

Yield: 2.0 g (40% of theory) of colorless crystals
MS (EI): 328, 300, 299, 283, 269
SF: C18H16O6 (328)

EXAMPLE 102

3-(1,4-Dihydroxybutyl)-4,11-dimethoxy-9-methyl-7H-dibenzo[b,g][1,5]dioxocin-5-one

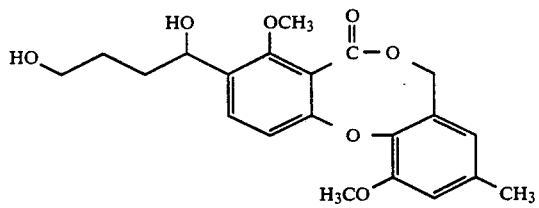

The primary ozonides prepared from 100 mg (0.26 mmol) of the compound from Example 89 by the process of Example 101 are reduced by addition of an excess of sodium borohydride.

SF: C21H24O7 (388)

EXAMPLE 103

3-methyl-11-methoxy-7H-dibenzo[b,g][1,5]dioxocin-5-one

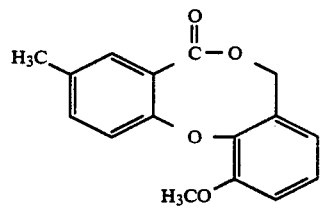

100 mg (0.32 mmol) of 2-(2-methoxy-6-chloromethyl)-5-methylphenoxybenzoic acid in 2 ml of absolute dimethylformamide and 54 mg (0.48 mmol) of 1,8-diazabicyclo[5.4.0]undec-7-ene are stirred at 80° C. under argon for 12 h. After evaporating in a high vacuum, the residue is taken up with methylene chloride, and the solution is washed with water, dried and evaporated. Chromatography on silica gel Si60 in methylene chloride yielded 17 mg (20% of theory) of colorless solid.

MS (EI): 270, 255, 241, 225
SF: $C_{16}H_{14}O_4$ (270)

EXAMPLE 104

11-Carboxymethyloxy-3-(1-formyloxy-3-methylbutyl)-4-methoxy-9-methyl-7H-dibenzo[b,g][1,5]dioxocin-5-one

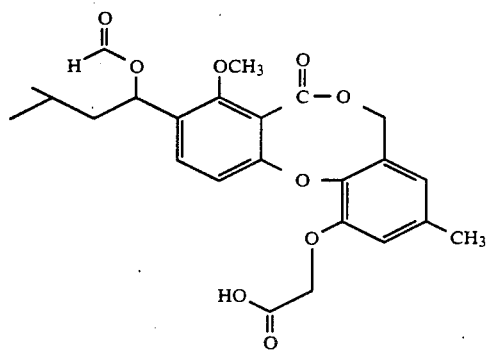

100 mg (0.2 mmol) Of the compound from Example 11 are stirred at 25° C. for 2 h in 2 ml of formic acid. After evaporating in a high vacuum, 90 mg (96% of theory) of colorless solid are obtained.

SF: $C_{24}H_{26}O_9$ (458)

$^1$H-NMR (δ ppm): 8.08 (1H, s); 7.48 (1H, d); 7.05 (1H, d); 6.70 (1H, s); 6.55 (1H, s); 6.28 (1H, mc); 5.7 (1H, broad); 5.60 (2H, mc); 4.8 (2H, s); 4.02 (3H, s); 2.38 (3H, s); 1.81 (1H, mc); 1.65 (1H, mc); 1.51 (1H, mc); 0.95 (6H, d).

EXAMPLE 105

3-(1-Hydroxy-3-methylbutyl)-4-methoxy-11-(2-hydroxy-3-methoxypropyloxy)-9-methyl-7H-dibenzo[b,g][1,5]dioxocin-5-one

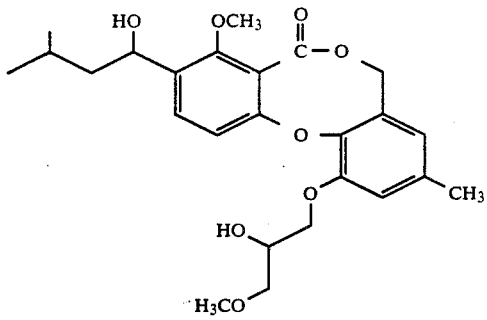

100 mg (0.23 mmol) of the compound from Example 24 are stirred at 25° C. for 2.5 h in 1% strength methanolic sulphuric acid. After diluting with methylene chloride, the mixture is washed with water and aqueous bicarbonate. After drying, evaporating and chromatography on silica gel Si60 in diethyl ether, 22 mg (20% of theory) of colorless solid are obtained.

MS (EI): 460, 389
SF: $C_{25}H_{32}O_8$ (460)

EXAMPLE 106

11-(2,3-Dihydroxy-propyloxy)-3-(1-hydroxy-3-methylbutyl)-4-methoxy-9-methyl-7H-dibenzo[b,g][1,5]dioxocin-5-one

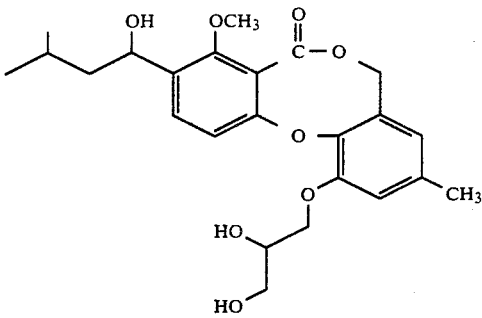

100 mg (0.23 mmol) of the compound from Example 24 are stirred at 25° C. for 12 h in 2 ml of tetrahydrofuran and 0.5 ml of aqueous 1% strength perchloric acid. After addition of methylene chloride, the mixture is washed with water and aqueous bicarbonate, dried and evaporated. After chromatography on silica gel Si60 in methylene chloride/methanol 95:5, 12 mg (11% of theory) of colorless solid are obtained.

MS (EI): 446, 389, 359, 353, 269, 179
SF: $C_{24}H_{30}O_8$ (446)

EXAMPLE 107 and Example 108

10-Bromo-11-hydroxy-3-(1-hydroxy-3-methylbutyl)-4-methoxy-9-methyl-7H-dibenzo[b,g][1,5]dioxocin-5-one (Example 108) and
8-bromo-11-hydroxy-3-(1-hydroxy-3-methylbutyl)-4-methoxy-9-methyl-7H-dibenzo[b,g][1,5]dioxocin-5-one(Example 107)

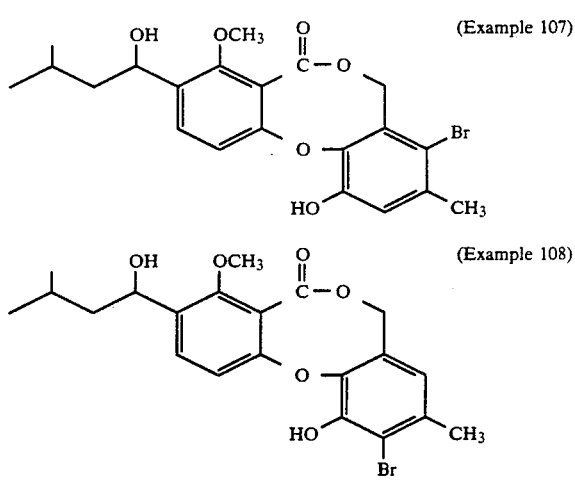

1 g (2.7 mmol) of penicillide (Ib) are stirred at 90° C. under argon with 0.8 g (5.7 mmol) of potassium carbonate and 2 ml (25 mmol) of bromonitromethane in 6 ml of dimethylformamide for 23 h. After evaporating in a high vacuum, the residue is taken up in 1N aqueous hydrochloric acid and extracted exhaustively with diethyl ether. After drying and evaporating, the residue is separated into two fractions on silica gel Si60 in methylene chloride/ethyl acetate 10:1 which, after evaporating in vacuo, are in each case subsequently separated on silica gel RP8 in acetonitrile/water 68:32 and, in addition to starting material, yield chromatographically uniform products.

EXAMPLE 107

Yield: 457 mg (37% of theory) of colorless solid
MS (EI): 452, 450, 395, 393, 349, 347, 179
SF: $C_{21}H_{23}O_6Br$ (451)

EXAMPLE 108

Yield: 36 mg (2.9% of theory) of colorless solid
MS (EI): 452, 450, 395, 393, 349, 347, 179
SF: $C_{21}H_{23}O_6Br$ (451)

In addition, 288 mg (20% of theory) of the compound (Example 107a) 8,10-dibromo-11-hydroxy-3-(1-hydroxy-3-methylbutyl)-4-methoxy-9-methyl-7H-dibenzo[b,g][1,5]dioxocin-5-one [Tetrahedron Letters 45, 3941, (1974)] are formed in the preparation of Examples 107 and 108.

EXAMPLE 109

4-Hydroxy-11-methoxy-9-methyl-3-(3-methyl-1-butanonyl)-7H-dibenzo[b,g][1,5]dioxocin-5-one

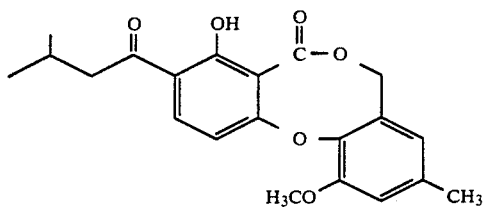

10.8 ml of a 1M boron tribromide solution in dichloromethane are added dropwise at −70° C. under argon to a solution of 6.2 g (16.1 mmol) of 3-(3-methyl-1-butanonyl)-4,11-dimethoxy-9-methyl-7H-dibenzo[b,g][1,5]-dioxocin-5-one in 160 ml of dichloromethane. After 1.5 h, 6 ml of methanol are added and the solution is brought to room temperature after a further 40 minutes. It is washed with sodium hydrogen carbonate solution and water, dried over magnesium sulphate and concentrated in vacuo. The residue is purified on a silica gel column using petroleum ether/ethyl acetate 6:1.

Yield: 4.0 g (67% of theory)
MS (EI): M+ =370
SF: $C_{21}H_{22}O_6$

The compounds shown in Table 11 are prepared analogously to the procedure for Example 109:

TABLE 11

| Ex. No. | $R^{12}$ | formula (EI) | SF |
|---|---|---|---|
| 110 | H | 356, 299, 221, 137 | $C_{20}H_{20}O_6$ (356) |
| 111 | —CH₂—CH₃ | 384, 165, 164, 149, 136 | $C_{22}H_{24}O_6$ (384) |

TABLE 11-continued

| Ex. No. | $R^{12}$ | formula (EI) | SF |
|---|---|---|---|
| 112 | —CH₂—CH(CH₃)CH₃ | 412, 221, 150, 136 | $C_{24}H_{28}O_6$ (412) |

EXAMPLE 113

4-Hydroxy-3-(1-hydroxy-3-methylbutyl)-11-methoxy-9-methyl-7H-dibenzo[b,g][1,5]dioxocin-5-one

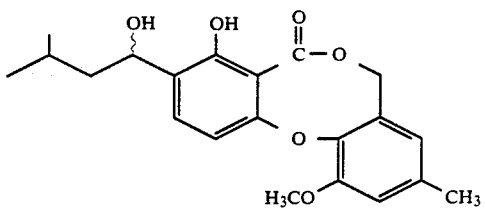

2.2 g (5.9 mmol) of the compound from Example 109 are dissolved in 40 ml of tetrahydrofuran, and 7 ml of glacial acetic acid and 0.96 g (15 mmol) of sodium cyanoborohydride are added. After 14 h at room temperature, the mixture is concentrated in vacuo, the residue is taken up in dichloromethane, and the solution is washed with sodium hydrogen carbonate solution and water, dried over magnesium sulphate and concentrated in vacuo. Purification is carried out by column chromatography on silica gel using dichloromethane/methanol 150/1 as the eluent.

Yield: 1.3 g (39% of theory)
MS (EI): M+ =372
SF: $C_{21}H_{24}O_6$

The compounds shown in the following Tables 12 and 13 were prepared analogously to the procedure for Example 113:

TABLE 12

| Ex. No. | $R^{12}$ | Formula (EI) | SF |
|---|---|---|---|
| 114 | H | 358, 301, 283, 165, 137 | $C_{20}H_{22}O_6$ (358) |
| 115 | —CH₂—CH₃ | 386, 368, 311, 165 | $C_{22}H_{26}O_6$ (386) |

TABLE 12-continued

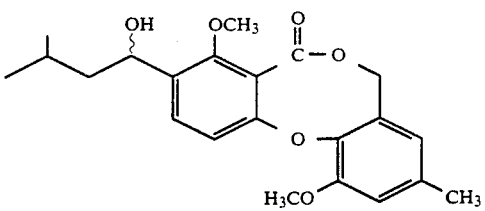

| Ex. No. | R[12] | Formula (EI) | SF |
|---|---|---|---|
| 116 | —CH₂—CH(CH₃)CH₃ | 414, 357, 339, 193 | C$_{24}$H$_{30}$O$_6$ (414) |

TABLE 13

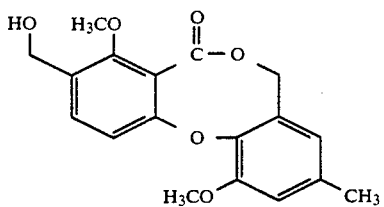

| Ex. No. | R[1] | Formula (EI) | SF |
|---|---|---|---|
| 117 | phenyl | 432, 345, 329, 303, 288 | C$_{27}$H$_{28}$O$_5$ (432) |
| 118 | —CH₂—phenyl | 446, 311, 239 | C$_{28}$H$_{30}$O$_5$ (446) |
| 119 | —CH=CH₂ | 382, 281, 175 | C$_{23}$H$_{26}$O$_5$ (382) |
| 120 | —CH₂—CH₃ | 384, 327, 177, 151 | |

EXAMPLE 121

3-[1-(R,S)-Hydroxy-3-methylbutyl]-4,11-dimethoxy-9-methyl-7H-dibenzo[b,g][1,5]dioxocin-5-one 158 g (0.41 mmol) of 3-(3-methyl-1-butanonyl)-4,11-dimethoxy-9-methyl-7H-dibenzo[b,g][1,5]dioxocin-5-one are dissolved in 2 ml of tetrahydrofuran and 0.1 ml of water. 23 mg (0.61 mmol) of sodium borohydride are added to the solution and the mixture is stirred overnight at room temperature. Excess sodium borohydride is destroyed by addition of a few drops of acetic acid. The mixture is concentrated in vacuo, the residue is taken up in dichloromethane and the solution is washed with water. The organic phase is dried over magnesium sulphate, concentrated and purified by column chromatography on silica gel using petroleum ether/diethyl ether 1:1.

Yield: 73% of theory
MS (EI): M$^+$ = 386
SF: C$_{22}$H$_{26}$O$_6$

EXAMPLE 122

4,11-Dimethoxy-3-hydroxymethyl-9-methyl-7H-dibenzo[b,g][1,5]dioxocin-5-one

The title compound was prepared analogously to the procedure for Example 121.
MS (EI): 330, 180, 150
SF: C$_{18}$H$_{18}$O$_6$ (330)

The compounds shown in the following Table 14 are prepared analogously to the procedure of Example 121:

TABLE 14

| Ex. No. | R[12] | Formula (EI) | SF |
|---|---|---|---|
| 123 | —CH(CH₃)CH₃ | 414, 315, 297, 151 | C$_{24}$H$_{30}$O$_6$ (414) |

TABLE 14-continued

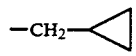

| Ex. No. | R[12] | Formula (EI) | SF |
|---|---|---|---|
| 124 | —CH₂—CH=CH₂ | 412, 355, 297, 151 | C$_{24}$H$_{28}$O$_6$ (412) |
| 125 | —CH₂-cyclopropyl | 426, 369, 297, 285, 269 | C$_{25}$H$_{30}$O$_6$ (426) |
| 126 | —CH₂—C(=O)—O—C(CH₃)₃ | DCI: 504 (M+NH₄+) 486, 469, 430, 413 | C$_{27}$H$_{34}$O$_8$ (486) |
| 127 | —CH₂—CH(CH₃)₂ | 428, 371, 315, 297, 151 | C$_{25}$H$_{32}$O$_6$ (428) |
| 128 | —CH₂—CH₃ | 400, 343, 297, 269 | C$_{23}$H$_{28}$O$_6$ (400) |
| 129 | —CH₂—C₆H₅ | 462, 405, 297, 269 | C$_{28}$H$_{30}$O$_6$ (462) |
| 130 | —CH₂—CH₂—CH₃ | 414, 357, 297, 151 | C$_{24}$H$_{30}$O$_6$ (414) |
| 131 | —CH₂—CH₂—C₆H₅ | DCI: 494 (M+NH₄+) 476, 459, 419, 355 | C$_{29}$H$_{32}$O$_6$ (476) |
| 132 | —CH(C₆H₅)₂ | FAB: 521, 355, 167 | C$_{34}$H$_{34}$O$_6$ (538) |
| 133 | —(CH₂)₄—Br | 508, 506, 451, 449, 297 | C$_{25}$H$_{21}$O$_6$Br (507) |
| 134 | —CH₂—CH(O—C(CH₃)₂—O—) | 486, 429, 371, 297, 269 | C$_{28}$H$_{36}$O$_8$ (486) |
| 135 | —CH₂—C₆H₄—OCH₃ | FAB: 515 (M+Na+), 492, 475, 355, 154 | C$_{29}$H$_{32}$O$_7$ (492) |
| 136 | —cyclopentyl | 440, 315, 297, 151 | C$_{26}$H$_{32}$O$_6$ (440) |
| 137 | —CH₂—C(=O)—NH₂ | 429, 412, 372, 353, 297 | C$_{23}$H$_{27}$NO$_7$ (429) |
| 138 | —CH₂—CH₂—Br | 480, 478, 462, 460, | C$_{23}$H$_{27}$BrO$_6$ (479) |

TABLE 14-continued

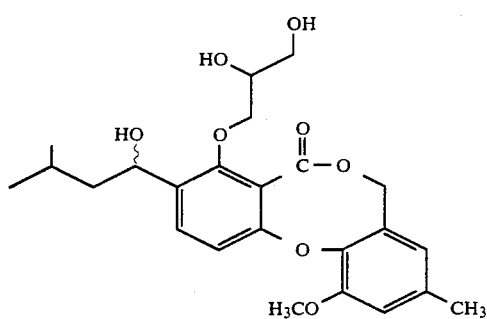

| Ex. No. | R$^{12}$ | Formula (EI) | SF |
|---|---|---|---|
| | | 343, 297 | |

EXAMPLE 139

3-(1-Hydroxy-3-methylbutyl)-4-(2,3-dihydroxypropoxy)-11-methoxy-9-methyl-7H-dibenzo[b,g][1,5]dioxocin-5-one

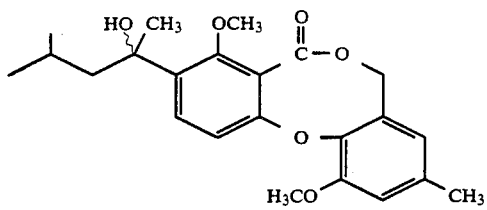

100 mg (0.21 mmol) of the compound from Example 134 are dissolved in 5 ml of 80% strength acetic acid. After a reaction time of 5 h at room temperature, the solution is concentrated in vacuo, and the residue is codistilled twice with toluene and purified by column chromatography on silica gel using dichloromethane/methanol 25:1.

Yield: 53 mg (58% of theory)
MS (EI): 446, 239, 151
SF: $C_{24}H_{30}O_8$ (446)

EXAMPLE 140

3-(1-Hydroxy-1,3-dimethylbutyl)-4,11-dimethoxy-9-methyl-7H-dibenzo[b,g][1,5]dioxocin-5-one 100 mg (0.26 mmol) of 4,11-dimethoxy-9-methyl-3-(3-methylbutan-1-onyl)-7H-dibenzo[b,g][1,5]dioxocin-5-one are dissolved in 5 ml of absolute tetrahydrofuran under argon and 0.2 ml (0.6 mmol) of a 3M methylmagnesium bromide solution in diethyl ether are added at room temperature. After 4 h, the reaction is discontinued by addition of 0.2 ml of ammonium chloride solution. The mixture is concentrated in vacuo, the residue is taken up in dichloromethane and the solution is washed with water. After drying the organic phase over magnesium sulphate, it is concentrated and the residue is purified by column chromatography on silica gel using petroleum ether/ethyl acetate 10:1.

Yield: 52 mg (50% of theory)
MS (EI): 400, 343, 283
SF: $C_{23}H_{28}O_6$ (400)

EXAMPLE 141

4-p-Chlorophenyl-3-(1-p-chlorophenyl-1-hydroxy-3-methylbutyl)-11-methoxy-9-methyl-7H-dibenzo[b,g][1,5]dioxocin-5-one

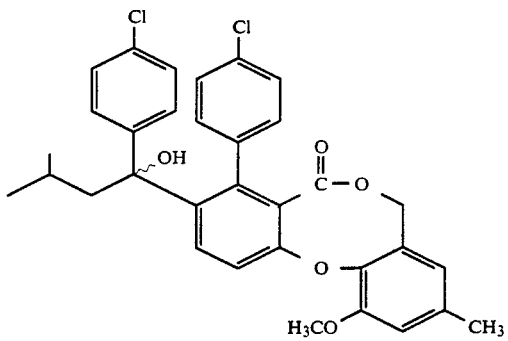

The title compound was prepared analogously to the procedure for Example 140.

Yield: 46% of theory
MS (EI): 578, 576, 519, 478, 363
SF: $C_{33}H_{30}Cl_2O_5$

The compounds shown in the following Tables 16 and 17 were prepared analogously to the procedure for Example 140.

TABLE 16

| Ex. No. | R$^1$ | Formula (EI) | SF |
|---|---|---|---|
| 142 | -⌬ (phenyl) | 430, 373, 329, 223 | $C_{27}H_{26}O_5$ (430) |

TABLE 16-continued

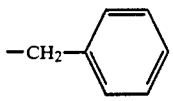

| Ex. No. | R[1] | Formula (EI) | SF |
|---|---|---|---|
| 143 | —CH₂—C₆H₅ | 444, 401 | C28H28O5 (444) |
| 144 | —CH=CH₂ | 380, 365, 323, 274, 173 | C23H24O5 (380) |
| 145 | —CH₂—CH₃ | 382, 339, 325, 201, 175, | C23H26O5 (382) |

TABLE 17

| Ex. No. | R[1] | Formula (EI) | SF |
|---|---|---|---|
| 146 | OCH₃ | 412, 355, 357, 311, 283, | C24H28O6 (412) |
| 147 | (allyl) | 408, 351, 323, 307, 278, | C25H28O5 (408) |

EXAMPLE 148

11-Ethoxy-4-methoxy-9-methyl-3-(3-methyl-1-methylenebutyl)-7H-dibenzo[b,g][1,5]dioxocin-5-one

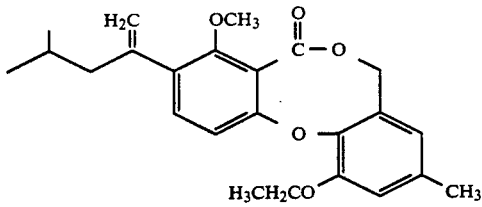

100 mg (0.25 mmol) of the compound from Example 66, dissolved in 4 ml of absolute tetrahydrofuran, are added dropwise under argon to a suspension of 150 mg (0.36 mmol) of methyltriphenylphosphonium bromide and sodium amide (instant ylide). After a reaction time of 14 h at room temperature, some acetone is added, the solid constituents are separated off and the solution is concentrated in vacuo. The residue is purified by column chromatography on silica gel using petroleum ether/ethyl acetate 6:1.
Yield: 28 mg (28% of theory)
MS (EI): 396, 232, 190
SF: C24H28O5 (396)

EXAMPLE 149

11-Ethoxy-3-(1-hydroxymethyl-3-methylbutyl)-4--methoxy-9-methyl-7H-dibenzo[b,g][1,5]dioxocin-5-one

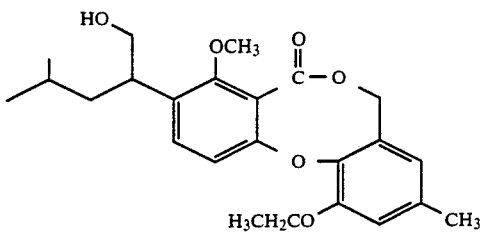

2 ml (1 mmol) of a 0.5 M 9-borabicyclo-3.3.1-nonane solution in hexane are added dropwise under argon to a solution of 130 mg (0.33 mmol) of the compound from Example 148 in 4 ml of absolute tetrahydrofuran. After 14 h at room temperature, a few drops of ethanol, 2 ml of 2 N sodium hydroxide solution and 0.5 ml of 30% strength hydrogen peroxide solution are added. The mixture is stirred vigorously for 3 h and then concentrated carefully and the residue is taken up in dichloromethane. The solution is washed with water, and the organic phase is dried over magnesium sulphate and concentrated, and the residue is purified by column chromatography on silica gel using petroleum ether/ethyl acetate 6:1.
Yield: 29 mg (20% of theory)
MS (EI): 414, 327, 163
SF: C24H30O6 (414)

Example 150

11-Hydroxy-3-(1-hydroxy-3-methylbutyl)-4-methoxy-9-methyl-10-prop-2-enyl-7H-dibenzo[b,g][1,5]dioxocin-5-one

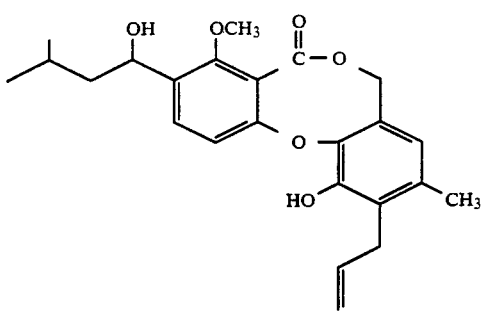

100 mg (0.25 mmol) of the compound from Example 20, dissolved in 2 ml of dimethylformamide, are heated to 160° C. under argon for 14 h. The solution is then concentrated, the residue is taken up in dichloromethane and the solution is washed with water. After concentrating the dichloromethane phase, the residue is purified by column chromatography on silica gel using petroleum ether/ethyl acetate 6:1.
Yield: 14 mg (14% of theory)
MS (EI): 412, 355, 325, 309
SF: C24H28O6 (412)

Example 151

11-Hydroxy-3-(1-hyroxy-3-methylbutyl)-4-methoxy-9-methyl-10-(1-phenyl-prop-1-enyl)-7H-dibenzo[b,g][1,5]-dioxocin-5-one

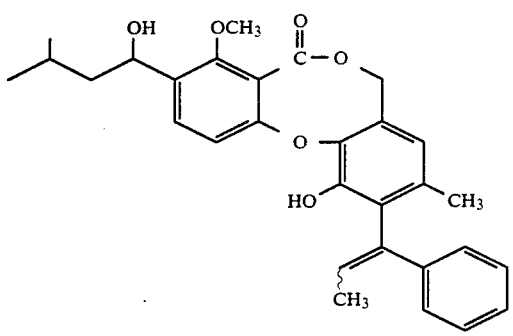

The title compound was prepared from Example 25 analogously to the procedure for Example 150.

MS (EI): 488, 431, 385, 150

SF: $C_{30}H_{32}O_6$ (448)

Example 152

4-p-Chlorophenyl-3-(3-methyl-1-butanonyl)-11-methoxy-9-methyl-7H-dibenzo[b,g][1,5]dioxocin-5-one

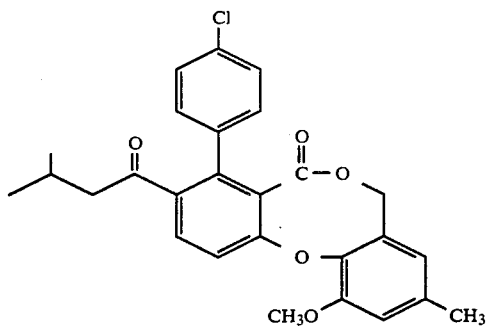

The title compound was prepared from 4,11-dimethoxy-9-methyl-3-(3-methylbutan-1-onyl)-7H-dibenzo[b,g][1,5]dioxocin-5-one analogously to the procedure of Example 140.

MS (EI): 464, 407

SF: $C_{27}H_{25}ClO_5$ (464)

Example 153

4-p-Chlorophenyl-3-(1-hydroxy-3-methylbutyl)-11-methoxy-9-methyl-7H-dibenzo[b,g][1,5]dioxocin-5-one

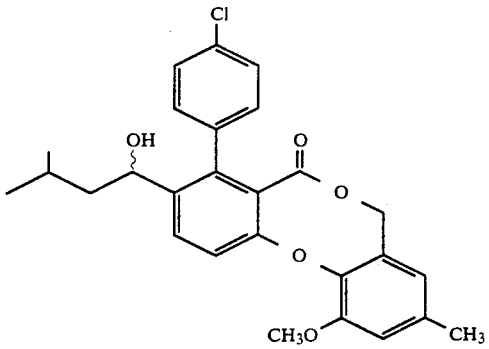

The title compound was prepared from Example 152 analogously to the procedure of Example 121.

MS (EI): 466, 409, 279, 363, 322

SF: $C_{27}H_{27}ClO_5$ (466)

The compounds shown in Table 18 were prepared in analogy to the procedure of Example 1:

TABLE 18

| Ex. No. | $R^1$ | $R^{15}$ | $R^6$ | $R^8$ | Formula (EI) | SF |
|---|---|---|---|---|---|---|
| 154 | ⟨isobutyl-OH⟩ | H | H | $OCH_3$ | 372, 315, 269, 243, 228 | $C_{21}H_{24}O_6$ |
| 155 | ⟨isobutyl-OH⟩ | H | $CH_3$ | H | 356, 299, 269, 253, 227 | $C_{21}H_{24}O_5$ (356) |
| 156 | ⟨isobutenyl⟩ | H | Br | $OCH_3$ | 434, 432, 389, 218, 203 | $C_{21}H_{21}BrO_5$ (433) |
| 157 | ⟨isobutyl-OH⟩ | $CH_3$ | $CH_3$ | $OCH_3$ | 400, 343, 325, 297, 149 | $C_{23}H_{28}O_6$ (418) |

Example 158

4,11-Dimethoxy-8,9-dimethyl-3-(1-hydroxy-3-methylbutyl)-7H-dibenzo[b,g][1,5]dioxocin-5-one

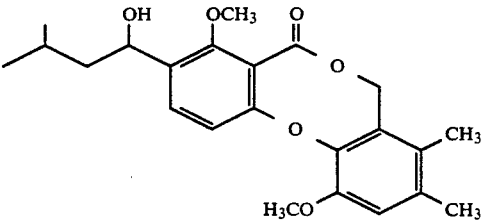

3.3 mmol of zinc chloride (1M in diethyl ether) are added under inert gas to 3 mmol of methylmagnesium bromide (3M in diethyl ether), the mixture is stirred at 25° C. for 10 min, a solution of 0.15 mmol of the compound of Example 39 in 3 ml of anhydrous tetrahyrofuran/6 ml of dimethyl sulphoxide is added, 5 mg of bis-(triphenylphosphine)-palladium(II) chloride are added and the mixture is stirred overnight at 50° C. It is hydrolyzed using 0.05 ml of 5N hydrochloric acid and taken up in water/ether, and the solution is washed 3 times with ether, and the organic phase is washed with water, dried ($Na_2SO_4$) and chromatographed on a silica gel column (methylene chloride/methanol 100:1) and then on an RP 8 column (acetonitrile/water 5:6). Yield: 10.1 mg of oil (16.3% of theory)

MS (EI): 400, 343, 297, 256
SF: $C_{23}H_{28}O_6$ (400)

Example 159

4,11-Dimethoxy-3-(1-hydroxy-3-methylbutyl)-8,9,10-trimethyl-7H-dibenzo[b,g][1,5]dioxocin-5-one

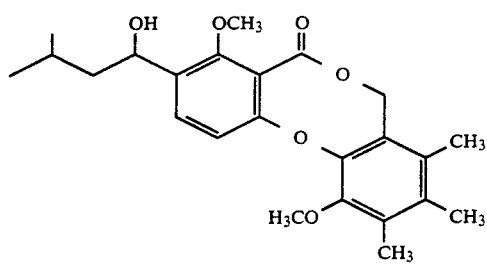

Starting from the compound of Example 41, the title compound is obtained analogously to Example 158.
Yield: 65% of theory
MS (EI): 414, 357, 339, 311, 270, 179
SF: $C_{24}H_{30}O_6$ (414)

Example 160

10-Bromo-11-methoxy-3-(1-hydroxy-3-methylbutyl)-4-ethenyl-9-methyl-7H-dibenzo[b,g][1,5]dioxocin-5-one

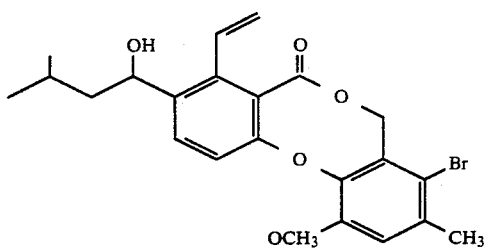

The title compound was prepared from Example 39 in analogy to the procedures of Examples 65, 78 and 121.
MS (EI): 462, 460, 405, 381, 359
SF: $C_{23}H_{25}BrO_6$ (461)

Example 161

8-Bromo-4,11-dimethoxy-3-(1-hydroxy-1-ethenyl-3-methylbutyl)-9-methyl-7H-dibenzo[b,g][1,5]dioxocin-5-one

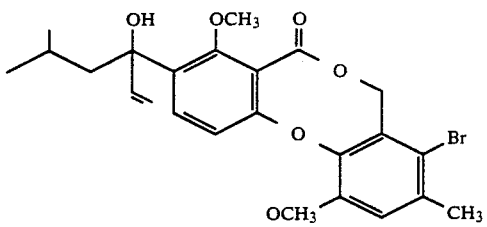

The title compound was prepared from Example 39 analogously to the procedure of Example 65 and, subsequently, of Example 78.
MS (EI): 492, 490, 435, 433, 363, 361
SF: $C_{24}H_{27}BrO_6$ (491)

Example 162

8-Ethenyl-11-hydroxy-3-(1-hydroxy-3-methylbutyl)-4-methoxy-9-methyl-7H-dibenzo[b,g][1,5]dioxocin-5-one

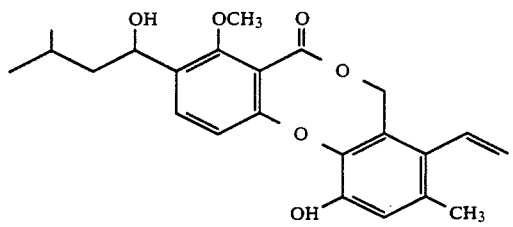

170 mg (0.38 mmol) of the compound from Example 108 in 7 ml of toluene are heated under reflux for 22 h under inert gas with 18 mg (0.015 mmol) of tetrakis(triphenylphosphine)-palladium and 0.2 ml (0.75 mmol) of tributylvinyltin. The suspension is adsorbed on silica gel and fractionally eluted using petroleum ether:ether=2:1. 116 mg (77% of theory) of colorless solid are obtained.
MS (EI): 398, 341, 323
SF: $C_{23}H_{26}O_6$ (398)

The compounds shown in Table 19 were prepared analogously to the procedure of Example 162:

TABLE 19

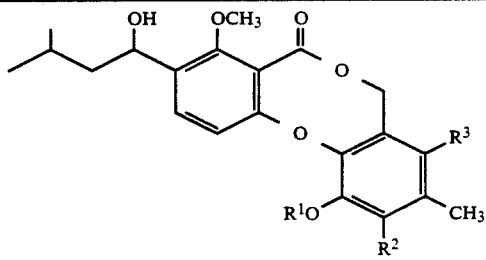

| Ex. No. | $R^1$ | $R^2$ | $R^3$ | Formula (EI) | SF |
|---|---|---|---|---|---|
| 163 | $CH_3$ | H | —CH=$CH_2$ | 412, 383, 355, 337 | $C_{24}H_{28}O_6$ |

TABLE 19-continued
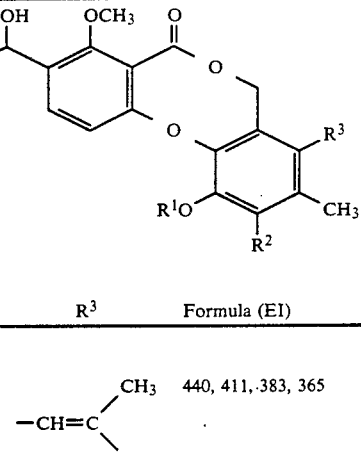
| Ex. No. | R¹ | R² | R³ | Formula (EI) | SF |
|---|---|---|---|---|---|
|  |  |  |  |  | (412) |
| 164 | $CH_3$ | H | 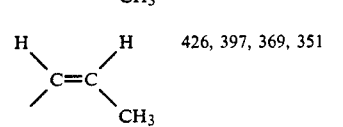 | 440, 411, 383, 365 | $C_{26}H_{32}O_6$ (440) |
| 165 | $CH_3$ | H | 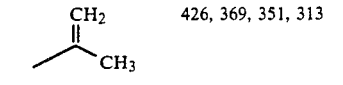 | 426, 397, 369, 351 | $C_{25}H_{30}O_6$ (426) |
| 166 | $CH_3$ | H | 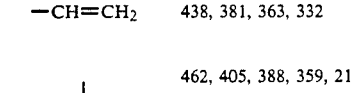 | 426, 369, 351, 313 | $C_{25}H_{30}O_6$ (426) |
| 167 | $CH_3$ | —CH=CH₂ | —CH=CH₂ | 438, 381, 363, 332 | $C_{26}H_{30}O_6$ (438) |
| 168 | $CH_3$ | H |  | 462, 405, 388, 359, 210 | $C_{28}H_{30}O_6$ (462) |
| 169 | $CH_3$ | H | 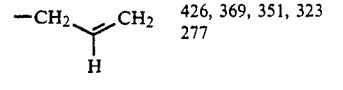 | 426, 369, 351, 323, 277 | $C_{25}H_{30}O_6$ (426) |
| 170 | H | —CH=CH₂ | —CH=CH₂ | 424, 395, 367, 349 | $C_{25}H_{28}O_6$ (424) |
The compounds shown in Table 20 were prepared in analogy to the procedure of Example 70:
TABLE 20
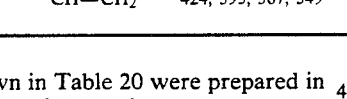
| Ex. No. | R¹ | R⁵ | Formula (EI) | SF |
|---|---|---|---|---|
| 171 | 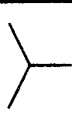 | 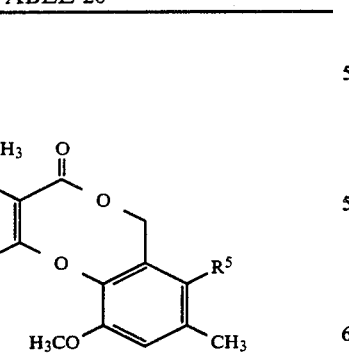 | 414, 396, 367, 357, 311 | $C_{28}H_{34}O_8$ (484) |
TABLE 20-continued
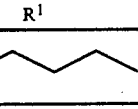
| Ex. No. | R¹ | R⁵ | Formula (EI) | SF |
|---|---|---|---|---|
| 172 | 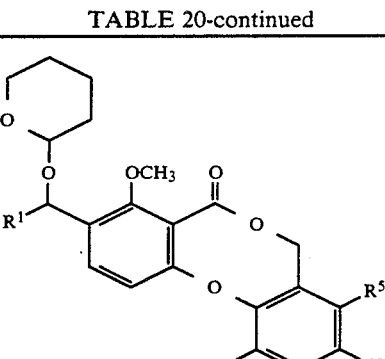 | H | 496, 412, 329, 299, 283 | $C_{29}H_{36}O_7$ (496) |

Example 173

4,11-dimethoxy-3-(1-hydroxy-3-methylbutyl)-8-oxomethylene-9-methyl-7H-dibenzo[b,g][1,5]dioxocin-5-one

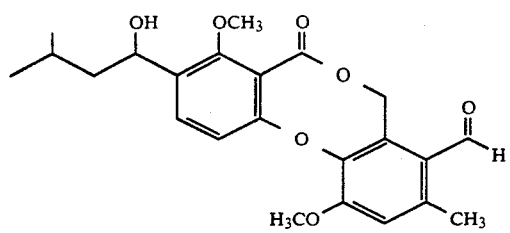

The title compound was prepared from Example 162 analogously to the procedure of Example 101.
MS (EI): 414, 385, 357, 327, 311
SF: $C_{23}H_{26}O_7$ (414)

Example 174

8-Azidomethylene-4-11,dimethoxy-3-(1-hydroxy-3-methylbutyl)-9-methyl-7H-dibenzo[b,g][1,5]dioxocin-5-one

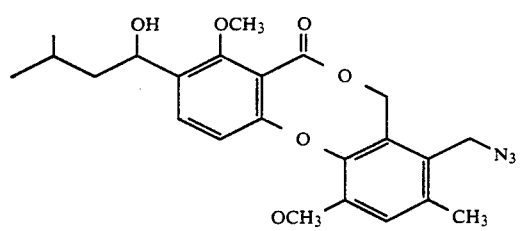

The title compound was prepared from the compound of Example 173 analogously to the procedure of Example 72 by coupling and subsequent removal of a silyl protecting group according to standard methods (see J. Amer. Chem. Soc. 94, 6190 (1972)).
MS (EI): 441, 384, 341, 161, 28
SF: $C_{23}H_{27}N_3O_6$ (441)

Example 175

8-Aminomethylene-4,11-dimethoxy-3-(1-hydroxy-3-methylbutyl)-9-methyl-7H-dibenzo[b,g][1,5]dioxocin-5-one

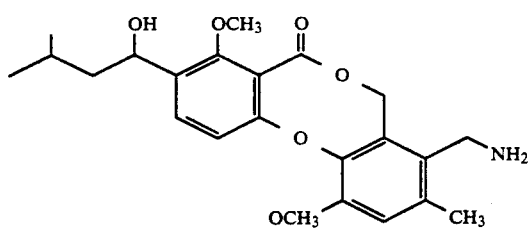

The compound was prepared from the compound of Example 174 analogously to the procedure of Example 74 by coupling and removal of a silyl protecting group according to standard methods (see J. Amer. Chem. Soc. 94, 6190 (1972)).
MS (DCI): 416, 398, 384, 176, 162
SF: $C_{23}H_{29}NO_6$ (415)

The compounds shown in Table 21 were prepared from the compound of Example 173 in analogy to the procedure of Example 78.

| Ex. | R | Formula (EI) | SF |
|---|---|---|---|
| 176 | OH, CH (CH₃) | 430, 373, 355, 337, 325 | $C_{27}H_{30}O_7$ (430) |
| 177 | OH, CH-C₆H₄-OCH₃ | 522, 504, 486, 455, 269 | $C_{30}H_{34}O_8$ (522) |
| 178 | OH, CH-biphenyl | 568, 550, 506, 315 Diastereomer I Diastereomer II | $C_{35}H_{36}O_7$ (568) |
| 179 | OH, CH-CH₂-CH₂-CH=CH₂ | 470, 452, 415, 395, 377 | $C_{27}H_{34}O_7$ (470) |
| 180 | OH, CH-CH(CH₃)₂ | 458 Diastereomer I Diastereomer II | $C_{26}H_{24}O_7$ (458) |
| 181 | OH, CH-phenyl | 492, 474, 435, 417, 389 | $C_{29}H_{32}O_7$ (492) |
| 182 | OH, CH-(CH₂)₃-CH=CH₂ | 498, 480, 441, 415, 397 | $C_{29}H_{38}O_7$ (498) |
| 183 | OH, CH-CH₂-CH(CH₃)₂ | 472, 454, 415, 397, 379 Diastereomer I 472, 454, 415, 379 Diastereomer II | $C_{27}H_{36}O_7$ (472) |

Example 184

4,11-Dimethyl-3-(1-hydroxy-3-methylbutyl)-8-hydroxymethylene-9-methyl-7H-dibenzo[b,g][1,5]dioxocin-5-one The title compound was prepared from the compound of Example 173 analogously to the procedure of Example 121.

MS (EI): 416, 359, 341, 311, 297
SF: $C_{23}H_{28}O_7$ (416)

Example 185

4,11-Dimethoxy-3-(1-hydroxy-3-methylbutyl)-8-(2-ethoxycarbonylethenyl)-9-methyl-7H-dibenzo[b,g][1,5]dioxocin-5-one

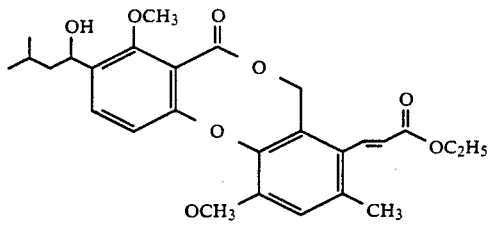

100 mg (0.24 mmol) of the compound from Example 173 are stirred under inert gas with 168 mg (0.48 mmol) of ethoxycarbonylmethylenetriphenylphosphorane in 3 ml of toluene at 80° C. for 14 h.

After addition of methylene chloride, the mixture is washed with 0.1 N aqueous hydrochloric acid, dried and evaporated. After chromatography on silica gel in methylene chloride containing 5% methanol, 103 mg (88% of theory) of colorless solid are obtained.
MS (DCI): 485 (M+H), 467, 427
SF: $C_{27}H_{32}O_8$ (484)

Example 186

4,11-Dimethoxy-3-(2-ethoxycarbonylethenyl)-9-methyl-7H-dibenzo[b,g][1,5]dioxocin-5-one

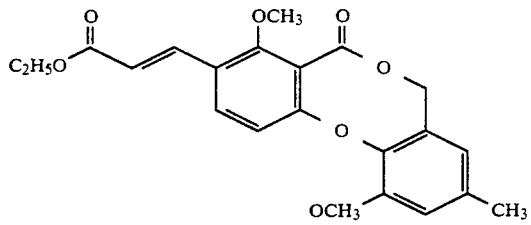

The title compound was prepared from the compound of Example 101 analogously to the procedure of Example 185.
MS (EI): 398, 353, 248
SF: $C_{22}H_{22}O_7$ (398)

Example 187

11-Hydroxy-3-(1-hydroxy-3-methylbutyl)-4-methoxy-9-methyl-8-nitro-7H-dibenzo[b,g][1,5]dioxocin-5-one

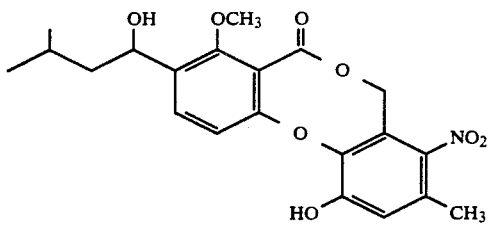

150 mg (0.4 mmol) of penicillide are dissolved in 15 ml of methylene chloride and stirred for 1 h under inert gas at a bath temperature of −68° C. after addition of 0.8 ml of a 0.5 molar solution of nitronium tetrafluoroborate. The reaction mixture is added to ice. After extraction with methylene chloride, washing with water and bicarbonate, drying and evaporating, the residue is chromatographed on silica gel in petroleum ether:ether=1:1. After evaporating, 86 mg (51% of theory) of yellowish solid are obtained.
MS (EI): 417, 399, 360, 342
SF: $C_{21}H_{23}NO_8$ (417)

Example 188

10-Bromo-11-hydroxy-3-(1-hydroxy-3-methylbutyl)-4-methoxy-9-methyl-8-nitro-7H-dibenzo[b,g][1,5]dioxocin-5-one

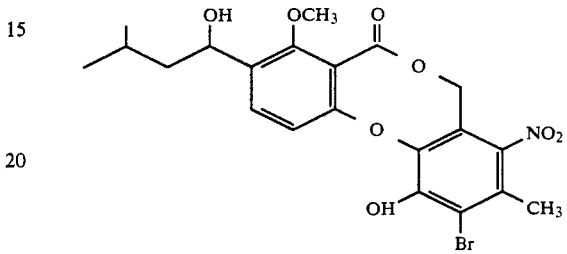

The title compound was prepared from the compound of Example 107 analogously to the method of Example 187.
MS (EI): 497, 495, 479, 477, 440, 438
SF: $C_{21}H_{22}NO_8$ (496)

Examples 189/190

8-Chloro-11-hydroxy-3-(1-hydroxy-3-methylbutyl)-4-methoxy-9-methyl-7H-dibenzo[b,g][1,5]dioxocin-5-one (189)

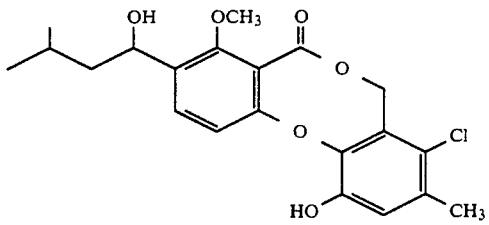

8,10-Dichloro-11-hydroxy-3-(1-hydroxy-3-methylbutyl)-4-methoxy-9-methyl-7H-dibenzo[b,g][1,5]dioxocin-5-one (190)

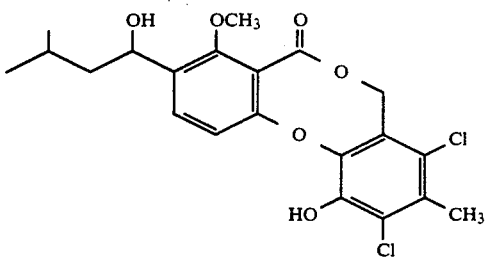

100 mg (0.27 mmol) of penicillide in 2 ml of ethanol:water=1:1 were stirred at 20° C. for 12 h after addition of 36 mg (0.27 mmol) of N-chlorosuccinimide and 70 mg (0.26 mmol) of iron(III) chloride hexahydrate. After extracting with methylene chloride, washing with water and drying, the mixture is fractionally chromatographed on silica gel in petroleum ether:ether=1:2.

Two chromatographically uniform products are obtained.

Example 189:

Yield 39 mg (=35% of theory) of colorless solid
MS (EI): 406, 349, 303
SF: $C_{21}H_{23}ClO_6$ (406)

Example 190:

Yield 50 mg (42% of theory) of colorless solid
MS (EI): 442, 440, 424, 422, 385, 383
SF: $C_{21}H_{22}Cl_2O_6$ (442)

Example 191

10-Iodo-11-hydroxy-3-(1-hydroxy-3-methylbutyl)-4-methoxy-9-methyl-7H-dibenzo[b,g][1,5]dioxocin-5-one

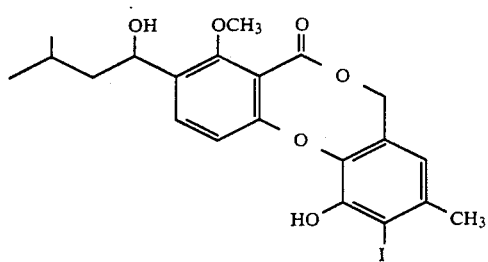

The title compound was prepared analogously to the procedure of Examples 189 and 190 using iodonium chloride as the halogenating reagent.
MS (EI): 498, 441, 395
SF: $C_{21}H_{23}IO_6$ (498)

Example 192

4,11-Dimethoxy-3-(1-hydroxy-3-methylbutyl)-8-iodo-9-methyl-7H-dibenzo[b,g][1,5]dioxocin-5-one

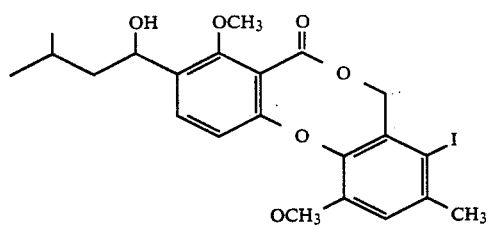

For the preparation of the title compound, penicillide is reacted analogously to the procedure of Example 9 to give the monomethyl ether and subsequently analogously to the procedure of Example 191.
MS (EI): 512, 455, 427, 409, 368
SF: $C_{22}H_{25}IO_6$ (512)

The compounds shown in table 22 were prepared analogously to the procedure for Example 9:

TABLE 22

| Ex. No. | $R^1$ | $R^2$ | Formula (EI) | SF |
|---|---|---|---|---|
| 192 | H | Cl | 420, 363, 345 | $C_{22}H_{25}ClO_6$ (420) |
| 194 | Cl | Cl | 456, 454, 399, 397 | $C_{22}H_{24}Cl_2O_6$ (456) |
| 195 | H | $NO_2$ | 431, 374 | $C_{22}H_{25}NO_8$ (431) |
| 196 | I | H | 512, 455, 409 | $C_{22}H_{25}JO_6$ (512) |

The compounds shown in Table 23 were prepared in analogy to the procedure of Example 78:

TABLE 23

| Ex. No. | $R^2$ | Formula (EI) | SF |
|---|---|---|---|
| 197 | OH, CH3-substituted phenyl with CH(CH3) | 448, 399, 301, 271, 242 | $C_{27}H_{28}O_6$ (448) |
| 198 | CH(OH)-phenyl-CH3 | 420, 402, 387, 361, 328 | $C_{25}H_{24}O_6$ (420) |
| 199 | CH(OH)-(o-CH3-phenyl) | 458, 420, 402, 387, 371 | $C_{25}H_{24}O_6$ (420) |
| 200 | CH(OH)-(CH2)3-CH=CH2 | 398, 329, 311, 299, 283 | $C_{23}H_{26}O_6$ (398) |
| 201 | CH(OH)-(o-OCH3-phenyl) | 436, 418, 403, 285, 135 | $C_{25}H_{24}O_7$ (436) |

TABLE 23-continued

[structure: R² substituted benzene with OCH3, C=O, O-CH2-benzene (H3CO, CH3)]

| Ex. No. | R² | Formula (EI) | SF |
|---|---|---|---|
| 202 | [1-(3-methoxyphenyl)-1-hydroxyethyl] | 436, 418, 403, 285, 135 | C25H24O7 (436) |
| 203 | [1-(2-phenylphenyl)-1-hydroxyethyl] | 482, 464, 449, 433, 419 | C30H26O6 (482) |
| 204 | [1-(4-methoxyphenyl)-1-hydroxyethyl] | 436, 418, 403, 327, 297 | C25H34O7 (436) |
| 205 | [1-(4-phenylphenyl)-1-hydroxyethyl] | 482, 464, 449, 359, 331 | C30H26O6 (482) |
| 206 | [1-(4-phenoxyphenyl)-1-hydroxyethyl] | 498, 480, 465, 347, 283 | C30H28O7 (500) |
| 207 | [1-hydroxy-7-octenyl] | 412, 339, 31, 299, 283 | C24H28O6 (412) |

It is understood that the specification and examples are illustrative but not limitative of the present invention and that other embodiments within the spirit and scope of the invention will suggest themselves to those skilled in the art.

Example 208

4,11-Dimethoxy-1-hydroxy-9-methyl-8(1-tetrahydropyranyl-2-oxy)oxymethylene)-7H-dibenzo[b,g][1,5-]dioxocin-5-one

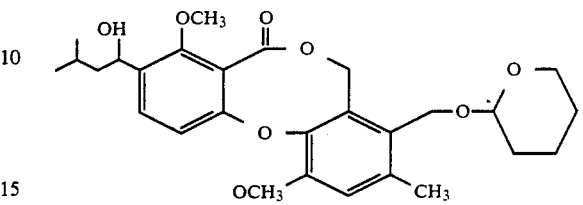

The title compound was prepared from the compound of example 184 by coupling and removal of a silyl protecting group according to standard methods (see J. Amer. Chem. Soc. 94, 6190 (1972)) in analogy to example 70.

MS (EI): 500, 399, 341
SF: C28H36O8 (500)

Example 209

3-(1-amino-3-methylbutyl)-8-bromo-4,11-dimethoxy-9-methyl-7H-dibenzo[b,g][1,5]dioxocin-5-one

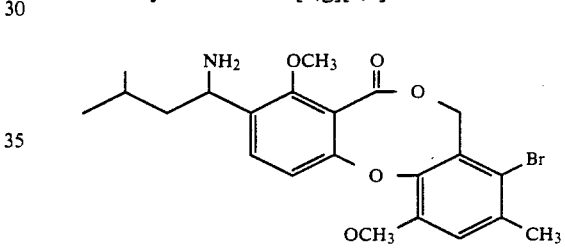

The title compound was prepared analogously to the procedures for example 72 and 74.

MS (DCI): 464, 462 (M+H), 449, 447, 408, 406
SF: C22H26BrNO5 (464)

Example 210

4,11-Dimethoxy-1-hydroxy-9-methyl-8-(1-pyrrolomethylen)-7H-debenzo[b,g][1,5]dioxocin-5-one

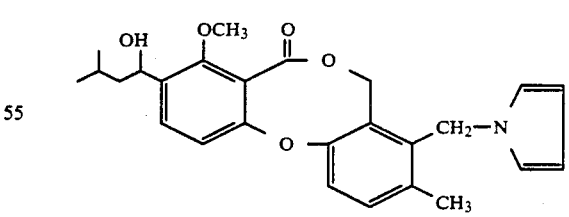

The title compound was prepared from the compound of example 174 by treatment with equimolar quantities of 2,5-Diethoxytetrahydrofuran and sodiumacetate in acetic acid for 15 min. at 100° C. and workup by standard extraction and chromatography.

MS (FAB): 472 (M⁺+Li)
SF: C27H31NO6 (465)

Example 211

3-(Methylsulfonylamido-3-methylbutyl)-8-bromo-4,11-dimethoxy-9-methyl-7H-dibenzo[b,g][1,5]dioxocin-5-one

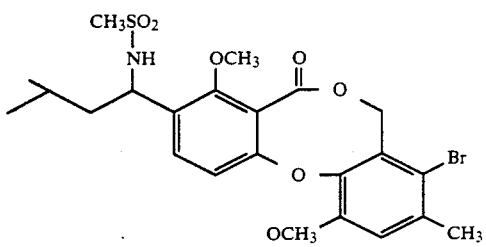

The title compound was prepared from the compound of example 209 analogously to example 77

MS (DCI): 561, 559 (M+ +NH$_4$+), 484, 486, 449, 447
SF: C$_{23}$H$_{28}$BrNSO$_7$ (542)

The compounds shown in table 24 were prepared analogously to the procedure of Example 101:

TABLE 24

| Example No. | R | MS (EI) | SF |
|---|---|---|---|
| 212 | —CO—OC$_2$H$_5$ | 458, 401, 355 | C$_{25}$H$_{30}$O$_8$ (458) |
| 213 | ⟨epoxide⟩—OC$_2$H$_5$ | 472, 458, 443, 429, 415, 401 | C$_{26}$H$_{32}$O$_8$ (472) |
| 214 | ⟨epoxide⟩—CH$_3$ | 442, 385, 467 | C$_{25}$H$_{30}$O$_7$ (442) |
| 215 | ⟨epoxide⟩—C$_6$H$_5$ | 504, 429, 251 | C$_{30}$H$_{32}$O$_7$ (507) |

Example 216

11-Hydroxy-3(1-hydroxy-3-methylbutyl)-4-methoxy-9-methyl-8(3-pyridyl)-7H-dibenzo[b,g][1,5]dioxocin-5-one-methoiodide

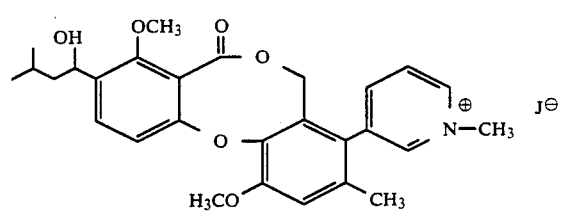

32.6 mg (0.07 mmol) of the compound from Example 224 were stirred with 3 ml iodmethane until the educt was consumed completely (TLC). Evaporation of excess iodomethane yielded 41 mg (96,5%) of the title compound.

SF: C$_{28}$H$_{32}$JNO$_6$ (605) MS (FAB) 478, 307, 242, 154

The compounds shown in Table 25 were prepared analogously to the procedure of Example 162:

TABLE 25

| Ex. No. | R$^1$ | R$^2$ | R$^3$ | MS (EI) | SF |
|---|---|---|---|---|---|
| 217 | CH$_3$ | H | —C≡C—C$_6$H$_5$ | 486, 383, 342, | C$_{30}$H$_{30}$O$_6$ (486) |
| 218 | CH$_3$ | H | =CH$_2$ / C—C$_6$H$_5$ | 488, 431, 413 | C$_{30}$H$_{32}$O$_6$ (488) |

TABLE 25-continued

[Structure: benzoate ester with OH, OCH3, isobutyl substituents on one ring and R1O, R2, R3, CH3 substituents on the benzyl ring]

| Ex. No. | R¹ | R² | R³ | MS (EI) | SF |
|---|---|---|---|---|---|
| 219 | $CH_3$ | H | 4-methylphenyl (–C₆H₄–CH₃) | 476, 419, 402 | $C_{29}H_{32}O_6$ (476) |
| 220 | $CH_3$ | H | 2-thienyl | 468, 411, 394 | $C_{26}H_{28}O_6S$ |
| 221 | $CH_3$ | H | 3-thienyl | 468, 411, 394, | $C_{26}H_{28}O_6S$ (468) |
| 222 | $CH_3$ | H | 3,4-dihydro-2H-pyran-6-yl | 468, 439, 437, 411 | $C_{27}H_{32}O_7$ (468) |
| 232 | $CH_3$ | H | $-C(=CH_2)-OC_2H_5$ | 456, 427, 425, 399 | $C_{26}H_{32}O_7$ (456) |
| 224 | $CH_3$ | H | 3-pyridyl | 463, 406, 388 | $C_{27}H_{29}NO_6$ (463) |
| 225 | $CH_3$ | H | $-C\equiv C-CH_2-N(morpholino)$ | 509, 478, 464 | $C_{29}H_{35}NO_7$ (509) |
| 226 | $CH_3$ | H | $-C\equiv C-CH_2-N(piperidino)$ | 507, 277, 189 | $C_{30}H_{37}NO_6$ (507) |
| 227 | $CH_3$ | H | cyclohex-1-en-1-yl | 466, 409, 391 | $C_{28}H_{34}O_6$ (466) |
| 228 | $CH_3$ | H | cyclopent-1-en-1-yl | 452, 423, 395, 377 | $C_{27}H_{32}O_6$ (452) |
| 229 | $CH_3$ | H | cyclobut-1-en-1-yl | 438, 409, 381, 363, 353 | $C_{26}H_{30}O_6$ (438) |
| 230 | $CH_3$ | H | 2-thiazolyl | 469, 412, 368 | $C_{25}H_{27}NO_6S$ (469) |

TABLE 25-continued

[Structure: Core scaffold with OH, OCH₃, carbonyl, OR¹, R², R³, and CH₃ substituents on aromatic rings]

| Ex. No. | R¹ | R² | R³ | MS (EI) | SF |
|---|---|---|---|---|---|
| 231 | CH₃ | H | (2-furyl, unsaturated) | 452, 395, 377 | $C_{26}H_{28}O_7$ (452) |
| 232 | CH₃ | H | (tetrahydrofuran-2-yl) | 454, 425, 397 | $C_{26}H_{30}O_7$ (454) |
| 233 | CH₃ | H | (3-furyl) | 452, 395, 377 | $C_{26}H_{28}O_7$ (452) |
| 234 | CH₃ | H | —S—CH₃ | 432, 375, 357 | $C_{23}H_{28}O_6S$ (432) |

The compounds shown in Table 26 were prepared by alkylation of the compound from example 184 following published procedures (e.g. A. F. Kluge et. al. J. Am. Chem. Soc. 94, 7827 (1972)), using established methods for introduction and removal of silyl protecting groups. (E. J. Corey et al, J. Am. Chem. Soc. 94, 6190 (1972).

TABLE 26

[Structure with OR group and OCH₃, CH₃ substituents]

| Ex. No. | R | SF | MS (EI) |
|---|---|---|---|
| 235 | —(CH₂)₂O(CH₂)₂OCH₃ | $C_{28}H_{38}O_9$ (518) | 518, 500, 398, 369, 341, 311 |
| 236 | —CH₃ | $C_{24}H_{30}O_8$ (430) | 430, 373, 341, 311 |
| 237 | —CH(CH₃)₂ | $C_{26}H_{34}O_7$ (458) | 458, 341, 311 |
| 238 | —CH₂—C₆H₄—OCH₃ | $C_{31}H_{26}O_8$ (536) | 536, 415, 163 |
| 239 | —CH₂—CH(CH₃)₂ | $C_{27}H_{36}O_7$ (472) | 472, 415, 341, 311 |

The compounds shown in Table 27 were prepared in analogy to the procedure of Example 162

[Structure with OH, OCH₃, carbonyl, CH₃O, and R substituents]

| Ex. No. | R | MS (EI) | SF |
|---|---|---|---|
| 240 | (3-methylbut-2-enyl) | 426, 369, 323, 282 | $C_{25}H_{30}O_6$ (426) |
| 241 | (but-2-enyl) | 412, 355, 309, 268 | $C_{24}H_{28}O_6$ (412) |
| 242 | (benzyl) | 448, 391, 345, 329, 320 | $C_{27}H_{28}O_6$ (448) |
| 243 | (4-methylbenzyl) | 462, 405, 359, 318 | $C_{28}H_{30}O_6$ (462) |
| 244 | (2-thienylmethyl) | 454, 351, 310 | $C_{25}H_{26}O_6S$ (454) |
| 245 | (3-thienylmethyl) | 454, 351, 315, 269 | $C_{25}H_{26}O_6S$ (454) |

-continued

| | | | |
|---|---|---|---|
| Ex. No. | R | MS (EI) | SF |
| 246 | (4-pyridyl-CH) | | $C_{26}H_{27}NO_6$ (449) |
| 247 | $CH_2$=C(CH₃)–Ph | 474, 377, 365 | $C_{29}H_{30}O_6$ (474) |
| 248 | (2-furyl-CH) | 438, 355, 315, 269 | $C_{25}H_{26}O_7$ (438) |
| 249 | (thiazolyl-CH) S,N | 455, 315, 269 | $C_{24}H_{25}NO_6S$ (455) |
| 250 | –S–CH₃ | | $C_{22}H_{26}O_6S$ |
| 251 | –CH=CH–CH₃ | 398, 341, 295, 254 | $C_{23}H_{26}O_6$ (398) |

The compounds shown in Table 28 were prepared from Example 251 analogously to the procedure of Example 78

TABLE 28

| Ex. No. | R | MS (EI) | SF |
|---|---|---|---|
| 252 | –CH₃ | 416, 359, 313, 272 | $C_{23}H_{28}O_7$ (416) |
| 253 | 4-Cl-C₆H₄– | 512, 455, 409 | $C_{28}H_{29}ClO_7$ (512,5) |
| 254 | C₆H₅– | 478, 421, 375 | $C_{28}H_{30}O_7$ |

Example 255

9-Formyl-3-(1-hydroxy-3-methylbutyl)-4,11-dimethoxy-7H-dibenzo[b,g][1,5]dioxocin-5-on

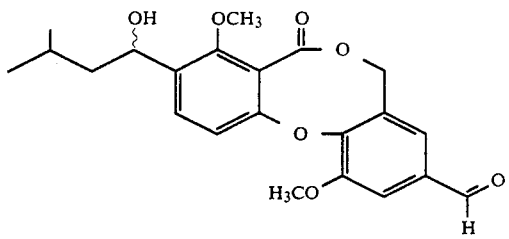

The title compound was prepared from Example 251 analogously to the procedure of Example 101.

MS (EI): 400, 382, 343, 297

SF: $C_{22}H_{24}O_7$ (400)

Example 256

9-(2-Carboxyethylester-ethenyl)-3-(1-hydroxy-3-methylbutyl)-4,11-dimethoxy-7H-dibenzo[b,g][1,5]dioxocin-5-on

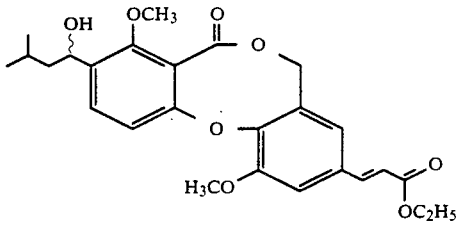

The title compound was prepared from Example 255 analogously to the procedure of Example 185.

MS (EI): 470, 452, 413, 383, 367

SF: $C_{26}H_{30}O_8$ (470)

Example 257

9-Hydroxymethyl-3-(1-hydroxy-3-methylbutyl)-4,11-dimethoxy-7H-dibenzo[b,g][1,5]dioxocin-5-on

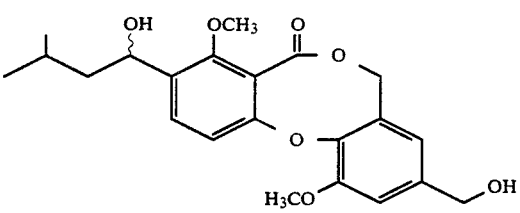

The title compound was prepared from Example 251 analogously to the procedure of Example 121

MS (EI): 402, 345, 299, 258

SF: $C_{22}H_{26}O_7$ (402)

Example 258

9-Bromo-3-(1-hydroxy-3-methylbutyl)-4,11-dimethoxy-7H-dibenzo[b,g][1,5]dioxocin-5-on

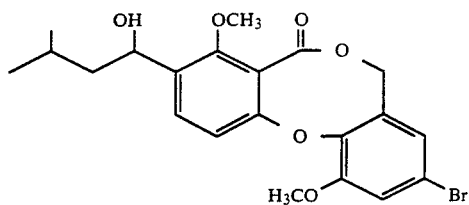

The title compound was prepared analogously to the procedure of Example 1

MS (EI): 452 (M+), 450, 395, 393, 349, 347
SF: $C_{21}H_{23}BrO_6$ (451)

We claim:

1. A compound of the formula

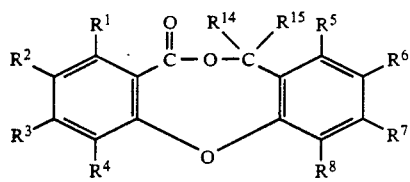

in which $R^1$, $R^2$, $R^3$, $R^4$, $R^5$, $R^6$, $R^7$ and $R^8$ are identical or different and in each case
represent hydrogen or
represent straight-chain or branched alkyl, alkylthio, alkenyl or alkynyl in each case having up to 12 carbon atoms, which are optionally substituted by halogen, azido, imino, hydroxyl-substituted imino, hydroxyl, cyano, cycloalkyl having 3 to 8 carbon atoms, or by phenyl or phenoxy, which in turn may be monosubstituted to trisubstituted by identical or different substituents from the group consisting of halogen, nitro, phenyl, phenoxy, cyano, straight-chain or branched alkyl, alkoxy or alkoxycarbonyl in each case having up to 8 carbon atoms, optionally substituted by hydroxyl, halogen, cycloalkyl having 3 to 8 carbon atoms, alkoxy or alkoxycarbonyl having up to 8 carbon atoms, or by phenyl, which in turn may be substituted by halogen, hydroxyl, alkyl, alkoxy or alkoxycarbonyl in each case having up to 8 carbon atoms, or nitro or cyano, or by a group of the formula $-NR^9R^{10}$, $-COR^{11}$ or $-OR^{12}$, or denotes phenyl, which is optionally substituted by halogen, hydroxyl, nitro or cyano, or $R^1$, $R^2$, $R^3$, $R^4$, $R^5$, $R^6$, $R^7$ and $R^8$ are identical or different and in each case
represent halogen, cyano, hydroxyl or nitro,
represent cycloalkenyl having 3 to 8 carbon atoms,
represent a group of the formula $-NR^9R^{10}$, $-COR^{11}$ or $-OR^{12}$, in which $R^9$ and $R^{10}$ are identical or different and in each case denote hydrogen, straight-chain or branched alkyl having up to 8 carbon atoms or phenyl, or a group of the formula $-S(O)_pR^{13}$ $R^{11}$ denotes hydrogen, hydroxyl, straight-chain or branched alkyl or alkoxy having up to 6 carbon atoms, phenoxy, phenyl or the group $-NR^9R^{10}$, $R^{12}$ denotes hydrogen, cyclopropyl, cyclobutyl, cyclopentyl, cyclohexyl, cycloheptyl, formyl, acyl having up to 6 carbon atoms, trifluoromethoxy or a group of the formula $-S(O)_p-R^{13}$, in which p denotes a number 1 or 2, $R^{13}$—denotes straight-chain or branched alkyl having up to 6 carbon atoms or the group $-NR^9-R^{10}$, or $R^{12}$ denotes straight-chain or branched alkyl or alkenyl having up to 8 carbon atoms, which is optionally monosubstituted to tetrasubstituted by identical or different radicals from the group consisting of bromine, cyclopropyl, cyclopentyl, cyclohexyl, alkoxy or alkyoxycarbonyl having up to 6 carbon atoms, or by phenyl which may in turn be substituted by fluorine, chlorine, bromine, hydroxyl, alkyl, alkoxy or alkoxycarbonyl in each case having up to 6 carbon atoms, nitro or cyano, or is substituted by a group of the formula $-NR^9R^{10}$, $-COR^{11}$ or $-OR^{12}$, or $R^1$ or $R^2$, $R^2$ and $R^3$, $R^3$ and $R^4$, $R^5$ and $R^6$, $R^6$ and $R^7$, or $R^7$ and $R^8$ in each case together form a saturated or unsaturated 5- to 7-membered carbocycle which is optionally substituted by nitro, cyano, hydroxyl, straight-chain or branched alkyl having up to 8 carbon atoms, or by a group of the formula $-NR^9R^{10}$, $-COR^{11}$ or $-OR^{12}$, $R^{14}$ and $R^{15}$ are identical or different and in each case denote hydrogen, or straight-chain or branched alkyl having up to 10 carbon atoms, which is optionally substituted by halogen, nitro, cyano, hydroxyl or a group of the formula $-NR^9R^{10}$, $-COR^{11}$ or $-OR^{12}$, denote phenyl, which is optionally substituted by nitro, cyano, halogen, alkyl, alkoxy or alkoxycarbonyl having up to 8 carbon atoms or by a group of the formula $-NR^9R^{10}$, or a physiologically acceptable salt thereof but a) $R^8$ may not denote hydroxyl, methoxy or acetyl if $R^1$ represents methoxy, $R^3$, $R^4$, $R^5$, $R^7$, $R^{14}$ and $R^{15}$ represent hydrogen, $R^6$ represents methyl and $R^2$ represents the group

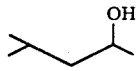

and b) $R^5$ and $R^7$ and not denote bromine and $R^8$ may not denote hydroxyl if $R^1$ represents methoxy, $R^3$, $R^4$, $R^{14}$ and $R^{15}$ represent hydrogen, $R^6$ represents methyl and $R^2$ represents the group

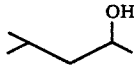

and c) $R^8$ may not denote methoxy if, $R^1$ represents methoxy, $R^3$, $R^4$, $R^5$, $R^7$, $R^{14}$ and $R^{15}$ represent hydrogen, $R^6$ represents methyl and $R^7$ represents the group

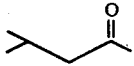

and d) $R^1$ may not denote methoxy if $R^3$, $R^4$, $R^5$, $R^6$, $R^{14}$ and $R^{15}$ represent hydrogen and $R^2$ represents the group of the formula

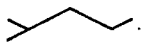

2. A compound or salt thereof according to claim 1, in which $R^1$, $R^2$, $R^3$, $R^4$, $R^5$, $R^6$, $R^7$ and $R^8$ are identical or different and in each case represent hydrogen or represent straight-chain or branched alkyl, alkylthio, alkenyl or alkynyl in each case having up to 10 carbon atoms, which are optionally monosubstituted to tetrasubstituted by identical or different radicals from the groups consisting of fluorine, chlorine, bromine, azido, imino, hydroxyl-substituted imino, hydroxyl, cyano, cyclopropyl, cyclopentyl and cyclohexyl, or are substituted by a group of the formula $-NR^9R^{10}$, $-COR^{11}$ or $-OR^{12}$, in which $R^9$ and $R^{10}$ are identical or different and in each case denote hydrogen, straight-chain or branched alkyl having up to 8 carbon atoms or phenyl, or a group of the formula $-S(O)_pR^{13}$ $R^{11}$ denotes hydrogen, hydroxyl, straight-chain or branched alkyl or alkoxy having up to 8 carbon atoms, phenoxy, phenyl or the group $-NR^9R^{10}$, $R^{12}$ denotes hydrogen, cyclopropyl, cyclobutyl, cyclopentyl, cyclohexyl, cycloheptyl, formyl, acyl having up to 6 carbon atoms, trifluoromethoxy or a group of the formula $-S(O)_p-R^{13}$, in which p denotes a number of 1 or 2, $R^{13}$—denotes straight-chain or branched alkyl having up to 6 carbon atoms or the group $-NR^9R^{10}$, or $R^{12}$ denotes straight-chain or branched alkyl or alkenyl having up to 8 carbon atoms, which is optionally monosubstituted to tetrasubstituted by identical or different radicals from the group consisting of bromine, cyclopropyl, cyclopentyl, cyclohexyl, alkoxy or alkoxycarbonyl having up to 6 carbon atoms, or by phenyl which may in turn be substituted by fluorine, chlorine, bromine, hydroxyl, alkyl, alkoxy or alkoxycarbonyl in each case having up to 6 carbon atoms, nitro or cyano, or is substituted by a group of the formula $-NR^9R^{10}$, $-COR^{11}$ or $-OR^{12}$, or $R^1$, $R^2$, $R^3$, $R^4$, $R^5$, $R^6$, $R^7$ and $R^8$ are identical or different and in each case represent fluorine, chlorine, bromine, iodine, cyano, hydroxyl, nitro or phenyl which is optionally substituted by fluorine, chlorine, bromine, phenyl, straight-chain or branched alkyl or alkoxy having up to 6 carbon atoms or hydroxyl, or represent cyclobutenyl, cyclopentenyl or cyclohexenyl, or represent a group of the formula $-NR^9R^{10}$, $-COR^{11}$ or $-OR^{12}$, or $R^1$ and $R^2$, $R^2$ and $R^3$, $R^3$ and $R^4$, $R^5$ and $R^6$, $R^6$ and $R^7$, or $R^7$ and $R^8$ together represent phenyl, cyclopentyl or cyclohexyl, and $R^{14}$ and $R^{15}$ are identical or different and in each case denote hydrogen, or straight-chain or branched alkyl having up to 8 carbon atoms, which is optionally substituted by fluorine, chlorine, bromine, cyano, hydroxyl or by a group of the formula $-NR^9R^{10}$, $-COR^{11}$ or $-OR^{12}$, or denote phenyl which is optionally substituted by nitro, cyano, fluorine, chlorine, bromine, alkyl, alkoxy or alkoxycarbonyl having up to 6 carbon atoms or by the group of the formula $-NR^9R^{10}$.

3. A compound or salt thereof according to claim 1, in which $R^1$, $R^2$, $R^3$, $R^4$, $R^5$, $R^6$, $R^7$ and $R^8$ are identical or different and in each case represent hydrogen or represent straight-chain or branched alkyl, alkylthio, alkenyl or alkynyl in each case having up to 8 carbon atoms, which are optionally monosubstituted to tetrasubstituted by identical or different radicals from the group consisting of fluorine, chlorine, bromine, iodine, azido, imino, hydroxyl-substituted imino, hydroxyl, cyclopropyl, cyclopentyl, cyclohexyl, or are substituted by phenyl, which in turn may be monosubstituted to trisubstituted by identical or different substituents from the group consisting of fluorine, chlorine, phenyl, phenoxy, and straight-chain or branched alkyl or alkoxy having up to 4 carbon atoms, or by a group of the formula $-NR^9R^{10}$, $-COR^{11}$ or $-OR^{12}$, in which $R^9$ and $R^{10}$ are identical or different and in each case denote hydrogen, straight-chain or branched alkyl having up to 6 carbon atoms or phenyl or a group of the formula $-S(O)_pR^{13}$ $R^{11}$ denotes hydrogen, hydroxyl, trifluoromethyl, straight-chain or branched alkyl or alkoxy having up to 6 carbon atoms, phenoxy, phenyl or the group $-NR^9R^{10}$, $R^{12}$ denotes hydrogen, cyclopropyl, cyclopentyl, cyclohexyl, cycloheptyl, formyl, acyl having up to 4 carbon atoms, trifluoromethoxy or a group of the formula $-S(O)_p-R^{13}$, in which p denotes a number 1 or 2, $R^{13}$—denotes straight-chain or branched alkyl having up to 4 carbon atoms, or denotes straight-chain or branched alkyl or alkenyl having up to 6 carbon atoms, which is optionally monosubstituted to trisubstituted by identical or different radicals from the group consisting of hydroxyl, fluorine, chlorine, bromine, cyclopropyl, cyclopentyl, cyclohexyl, alkoxy or alkoxycarbonyl having up to 4 carbon atoms or by phenyl which may in turn be substituted by fluorine, chlorine, hydroxyl or alkoxy having up to 4 carbon atoms, or by a group of the formula $-NR^9R^{10}$, $-COR^{11}$ or $-OR^{12}$, or $R^1$, $R^2$, $R^3$, $R^4$, $R^5$, $R^6$, $R^7$ and $R^8$ are identical or different and in each case represent fluorine, chlorine, bromine, iodine, hydroxyl or nitro, or represent phenyl which may in turn be substituted by fluorine, chlorine, methyl, isopropyl, phenyl or ethoxy, represent cyclobutenyl, cyclopentenyl or cyclohexenyl, represent a group of the formula $-NR^9R^{19}$, $-COR^{11}$ or $-OR^{12}$, and $R^{14}$ and $R^{15}$ are identical or different and denote hydrogen, straight-chain or branched alkyl having up to 6 carbon atoms or phenyl.

4. A compound according to claim 1, wherein such compound is 3-(1-hydroxy-3-methylbutyl)-4,11-dimethoxy-8-bromo-9-methyl-7H-dibenzo[b,g][1,5]dioxocin-5-one of the formula

5. A compound according to claim 1, wherein such compound is 3-(1-hydroxy-3-methylbutyl)-4-methoxy-9-methyl-7H-dibenzo[b,g][1,5]dioxocin-5-one of the formula

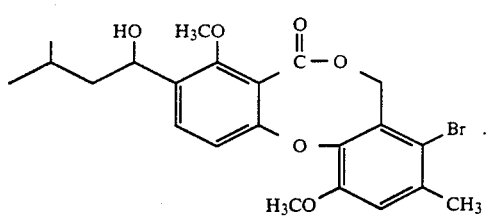

6. A compound according to claim 1, wherein such compound is 8-bromo-11-methoxy-3-(1-hydroxy-3-methylbutyl)-4-ethenyl-9-methyl-7H-dibenzo[b,g][1,5-]dioxocin-5-one of the formula

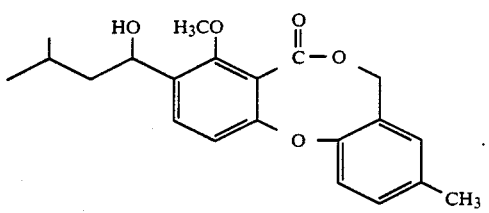

7. A compound according to claim 1, wherein such compound is 3-(1-hydroxy-3-methylbutyl)-4,11-dimethoxy-8-(1-methyl-ethenyl)-9-methyl-7H-dibenzo[b,g][1,5]dioxocin-5-one of the formula

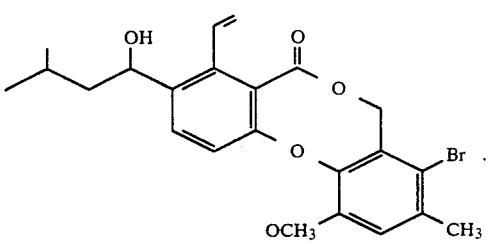

8. A compound according to claim 1, wherein such compound is 4,11-dimethoxy-3-(1-hydroxy-3-methylbutyl)-8-iodo-9-methyl-7H-dibenzo[b,g][1,5]dioxocin-5-one of the formula

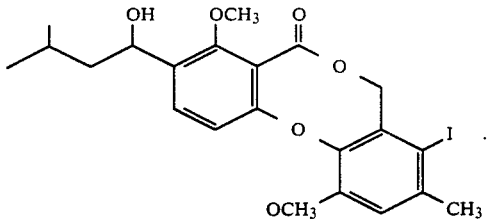

9. A compound according to claim 1, wherein such compound is 4,11-dimethoxy-3-(1-hydroxy-3-methylbutyl)-9-methyl-7H-dibenzo[b,g][1,5]dioxocin-5-one of the formula

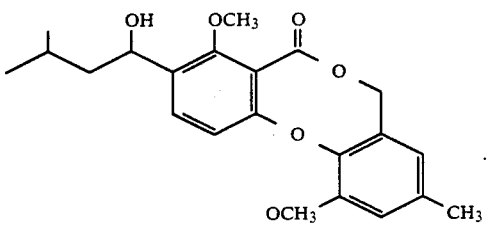

10. A compound according to claim 1, wherein such compound is 4,11-dimethoxy-3-(1-hydroxy-3-methylbutyl)-8-bromo-9-methyl-7H-dibenzo[b,g][1,5]dioxocin-5-one of the formula

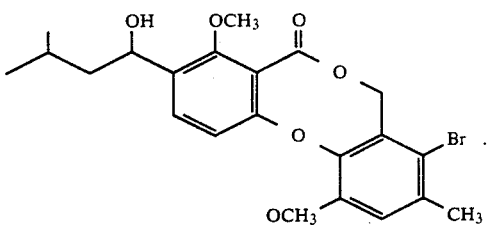

11. A circulation-active composition comprising an amount effective therefor of a compound or salt thereof according to claim 1 and a diluent.

12. A method of controlling the performance of the heart of a patient in need thereof with hypertension, cardiac insufficiency or digitalis poisoning which comprises administering to such patient an amount effective therefor of a compound of the formula

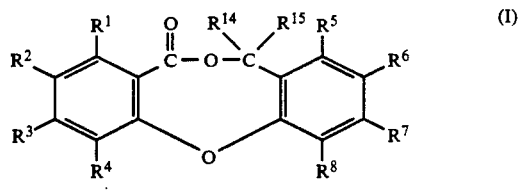

in which
$R^1$, $R^2$, $R^3$, $R^4$, $R^5$, $R^6$, $R^7$ and $R^8$ are identical or different and in each case
represent hydrogen or
represent straight-chain or branched alkyl, alkylthio, alkenyl or alkynyl in each case having up to 12 carbon atoms, which are optionally substituted by halogen, azido, imino, hydroxyl-substituted imino, hydroxyl, cyano, cycloalkyl having 3 to 8 carbon atoms, or by phenyl or phenoxy, which in turn may be monosubstituted to trisubstituted by identical or different substituents from the group consisting of halogen, nitro, phenyl, phenoxy, cyano, straight-chain or branched alkyl, alkoxy or alkoxycarbonyl in each case having up to 8 carbon atoms, optionally substituted by hydroxyl, halogen, cycloalkyl having 3 to 8 carbon atoms, alkoxy or alkoxycarbonyl having up to 8 carbon atoms, or by phenyl, which in turn may be substituted by halogen, hydroxyl, alkyl, alkoxy or alkoxycarbonyl in each case having up to 8 carbon atoms, or nitro or cyano, or by a group of the formula $-NR^9R^{10}$, $-COR^{11}$ or $-OR^{12}$, or denotes phenyl, which is optionally substituted by halogen, hydroxyl, nitro or cyano, or $R^1$, $R^2$, $R^3$, $R^4$, $R^5$, $R^6$, $R^7$ and $R^8$ are identical or different and in each case
represent halogen, cyano, hydroxyl or nitro,
represent cycloalkenyl having 3 to 8 carbon atoms,
represent a group of the formula $-NR^9R^{10}$, $-COR^{11}$ or $-OR^{12}$, or $R^1$ and $R^2$, $R^2$ and $R^3$, $R^3$ and $R^4$, $R^5$ and $R^6$, $R^6$ and $R^7$, or $R^7$ and $R^8$ in each case together form a saturated or unsaturated 5- to 7-membered carbocycle which is optionally substituted by nitro, cyano, hydroxyl, straight-chain or branched alkyl having up to 8 carbon atoms, or by a group of the formula $-NR^9R^{10}$, $-COR^{11}$ or $-OR^{12}$, $R^{14}$ and $R^{15}$ are identical or different and in each case denote hydrogen, or straight-chain or branched alkyl having up to 10 carbon atoms, which is optionally substituted by halogen, nitro, cyano, hydroxyl or a group of the formula $-NR^9R^{10}$, $-COR^{11}$ or $-OR^{12}$, denote phenyl, which is optionally substituted by nitro, cyano, halogen, alkyl, alkoxy or alkoxycarbonyl having up to 8 carbon atoms or by a group of the formula $-NR^9R^{10}$, or a physiologically acceptably salt thereof.

13. A method of controlling the performance of the heart of a patient in need thereof with hypertension, cardiac insufficiency or digitalis poisoning which comprises administering to such patient and amount effective therefor of a compound or salt thereof according to claim 1.

14. The method according to claim 12, wherein such compound is 3-(1-hydroxy-3-methylbutyl)-4,11-dimethoxy-8-bromo-9-methyl-7H-dibenzo[b,g][1,5]dioxocin-5-one, 3-(1-hydroxy-3-methylbutyl)-4-methoxy-9-methyl-7H-dibenzo[b,g][1,5]dioxocin-5-one, 8-bromo-11-methoxy-3-(1-hydroxy-3-methylbutyl)-4-ethenyl-9-methyl-7H-dibenzo[b,g][1,5]dioxocin-5-one, 3-(1-hydroxy-3-methylbutyl)-4,11-dimethoxy-8-(1-methyl-ethenyl)-9-methyl-7H-dibenzo[b,g][1,5]dioxocin-5-one, 4,11-dimethoxy-3-(1-hydroxy-3-methylbutyl)-8-iodo-9-methyl-7H-dibenzo[b,g][1,5]dioxocin-5-one, 4,11-dimethoxy-3-(1-hydroxy-3-methylbutyl)-9-methyl-7H-dibenzo[b,g][1,5]dioxocin-5-one, or 4,11-dimethoxy-3-(1-hydroxy-3-methylbutyl)-8-bromo-9-methyl-7H-dibenzo[b,g][1,5]dioxocin-5-one.

* * * * *

UNITED STATES PATENT AND TRADEMARK OFFICE
CERTIFICATE OF CORRECTION

PATENT NO. : 5,089,487
DATED : February 18, 1992
INVENTOR(S) : Frobel et al.

It is certified that error appears in the above-identified patent and that said Letters Patent is hereby corrected as shown below:

Title Page          ABSTRACT: Line 3 after " $R^1$ " delete " and " and substitute -- to --

Col. 86, line 17    After " $R^1$ " delete " or " and substitute -- and --

Col. 86, line 46    After " $R^7$ " delete " and " and substitute -- may --

Col. 87, line 32    Before " 1 " delete " of "

Col. 88, line 59    Delete " $-NR^9R^{19}$ " and substitute -- $-NR^9R^{10}$ --

Col. 90, line 10    Delete "  " and substitute -- 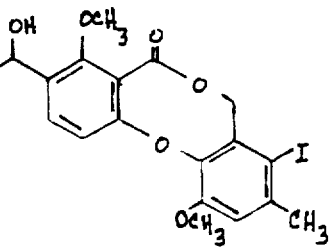 --

UNITED STATES PATENT AND TRADEMARK OFFICE
CERTIFICATE OF CORRECTION

PATENT NO. : 5,089,487

DATED : February 18, 1992

INVENTOR(S) : Frobel et al.

It is certified that error appears in the above-identified patent and that said Letters Patent is hereby corrected as shown below:

Col. 90, line 24   Delete " 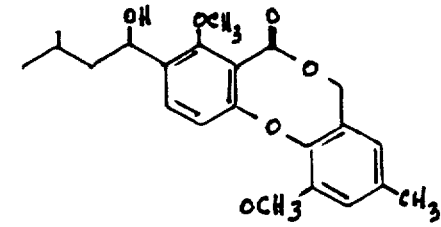 " and substitute -- 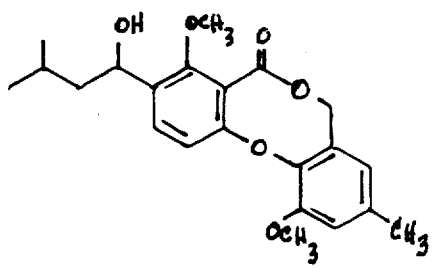 --

Col. 90, line 39   Delete " 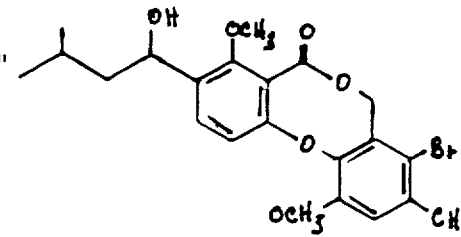 " and sub-

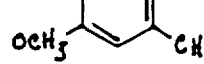

UNITED STATES PATENT AND TRADEMARK OFFICE
CERTIFICATE OF CORRECTION

PATENT NO. : 5,089,487

DATED : February 18, 1992

INVENTOR(S) : Frobel et al.

It is certified that error appears in the above-identified patent and that said Letters Patent is hereby corrected as shown below:

Col. 90, line 39 Cont'd stitute -- 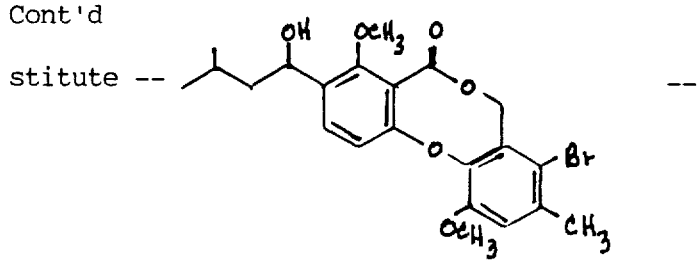 --

Signed and Sealed this

Ninth Day of November, 1993

Attest:

BRUCE LEHMAN

Attesting Officer     Commissioner of Patents and Trademarks